(12) United States Patent
Rodriguez Cutillas et al.

(10) Patent No.: US 9,747,412 B2
(45) Date of Patent: Aug. 29, 2017

(54) METHOD FOR IDENTIFYING ACTIVATION OF TRANSFERASES

(75) Inventors: Pedro Rodriguez Cutillas, Charterhouse Square (GB); Bart Vanhaesebroeck, Charterhouse Square (GB); Luisa Marie Beltran, Charterhouse Square (GB)

(73) Assignee: HVIVO SERVICES LIMITED, London (GB)

( * ) Notice: Subject to any disclaimer, the term of this patent is extended or adjusted under 35 U.S.C. 154(b) by 1111 days.

(21) Appl. No.: 13/880,447

(22) PCT Filed: Oct. 18, 2011

(86) PCT No.: PCT/GB2011/001497
§ 371 (c)(1),
(2), (4) Date: Aug. 5, 2013

(87) PCT Pub. No.: WO2012/052711
PCT Pub. Date: Apr. 26, 2012

(65) Prior Publication Data
US 2013/0303386 A1 Nov. 14, 2013

(30) Foreign Application Priority Data
Oct. 20, 2010 (GB) .................................. 1017721.0

(51) Int. Cl.
G06F 19/18 (2011.01)
C12Q 1/48 (2006.01)
G01N 33/68 (2006.01)

(52) U.S. Cl.
CPC .............. *G06F 19/18* (2013.01); *C12Q 1/48* (2013.01); *C12Q 1/485* (2013.01); *G01N 33/6842* (2013.01)

(58) Field of Classification Search
None
See application file for complete search history.

(56) References Cited

U.S. PATENT DOCUMENTS

2005/0026171 A1* 2/2005 Hawkins .................. C12Q 1/66
435/6.11

FOREIGN PATENT DOCUMENTS

WO 2010040024 A2 4/2010
WO WO-2010119261 A1 10/2010

OTHER PUBLICATIONS

Alcolea et al. "In-Depth Analysis of Protein Phosphorylation by Multidimensional Ion Exchange Chromatography and Mass Spectrometry." *Meth. Mol. Biol.* 658(2010):111-126.

Alessi et al. "Molecular Basis for the Substrate Specificity of Protein Kinase B; Comparison with MAPKAP Kinase-1 and p70 S6 Kinase." *FEBS Lett.* 399(1996):333-338.

Bantscheff et al. "Quantitative Chemical Proteomics Reveals Mechanisms of Action of Clinical ABL Kinase Inhibitors." *Nat. Biotechnol.* 25.9(2007):1035-1044.

Blagoev et al. "Temporal Analysis of Phosphotyrosine-dependent Signaling Networks by Quantitative Proteomics." *Nat. Biotechnol.* 22.9(2004):1139-1145.

Bodenmiller et al. "Phosphoproteomic Analysis Reveals Interconnected System-Wide Responses to Perturbations of Kinases and Phosphatases in Yeast." *Sci. Signal.* 3.153(2010):rs4.

Cartlidge et al. "The tRNA Methylase METTL1 is Phosphorylated and Inactivated by PKB and RSK in vitro and in Cells." *EMBO J.* 24.9(2005):1696-1705.

Casado et al. "A Self-Validating Quantitative Mass Spectrometry Method for Assessing the Accuracy of High-content Phosphoproteomic Experiments." *Mol. Cell Prot.* 10(2011):1-11.

Dayon et al. "Relative Quantification of Proteins in Human Cerebrospinal Fluids by MS/MS Using 6-Plex Isobaric Tags." *Anal. Chem.* 80(2008):2921-2931.

Knebel et al. "A Novel Method to Identify Protein Kinase Substrates: eEF2 Kinase is Phosphorylated and Inhibited by SAPK4/p38δ." *EMBO J.* 20.16(2001):4360-4369.

Miller et al. "Linear Motif Atlas for Phosphorylation-Dependent Signaling." *Sci. Signal.* 1.35(2008):ra2.

Montoya et al. "Characterization of a TiO2 Enrichment Method for Label-Free Quantitative Phosphoproteomics." *Methods.* 54(2011):370-378.

Savitski et al. "Confident Phosphorylation Site Localization Using the Mascot Delta Score." *Technol. Innov. Resources.* 10(2011):1-12.

(Continued)

*Primary Examiner* — Marsha Tsay
(74) *Attorney, Agent, or Firm* — Mintz Levin Cohn Ferris Glovsky and Popeo, P.C.; Muriel Liberto, Esq.

(57) ABSTRACT

The present invention provides a method for identifying differential activation of a bisubstrate protein modifying enzyme between samples, comprising:
(i) incubating a first sample with x different concentrations of the non-protein substrate of said enzyme, wherein x is 2 or greater than 2;
(ii) quantifying modification of a polypeptide in said sample at each of the x different concentrations of the non-protein substrate;
(iii) determining the affinity of said enzyme for said non-protein substrate;
(iv) repeating steps (i) to (iii) for a second or subsequent sample; and
(v) comparing the affinity of said enzyme for said non-protein substrate between said samples;
wherein a difference in affinity of said enzyme for said non-protein substrate between samples is indicative of differential activation of said enzyme between samples. The present invention also provides a method for identifying an in vivo substrate of a bisubstrate protein modifying enzyme.

19 Claims, 16 Drawing Sheets

(56) References Cited

OTHER PUBLICATIONS

Figure 1A:
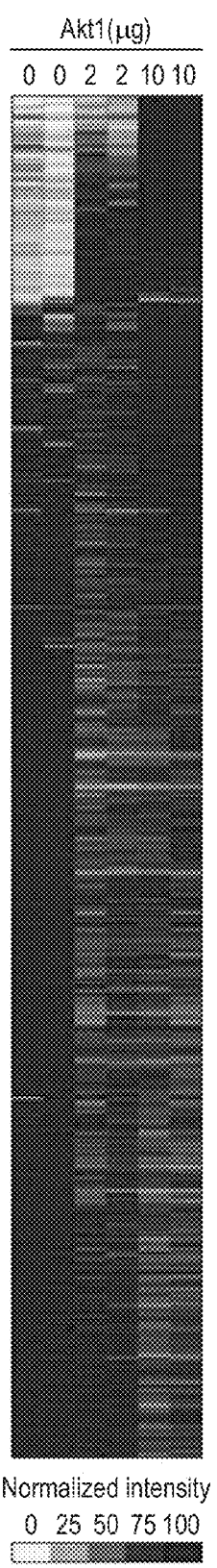

Kubota et al., Sensitive Multiplexed Analysis of Kinase Activities and Activity-based Kinase Identification, Nature Biotech. (2009) 27(10):933-940.
Luo et al., Global Impact of Oncogenic Src on a Phosphotyrosine Proteome, J Proteome Res. (2008) 7:3447-3460.
Cutillas et al., Ultrasensitive and absolute quantification of the phosphoinositide 3-kinase/Akt signal transduction pathway by mass spectrometry, Proc Natl Acad Sci (2006) 103(24):8959-8964.
Olsen et al., Global, In Vivo, and Site-Specific Phosphorylation Dynamics in Signaling Networks, Cell (2006) 127:635-648.
Alcolea et al., "Increased Confidence in Large-Scale Phosphoproteomics Data by Complementary Mass Spectrometric Techniques and Matching of Phosphopeptide Data Sets", J Proteome Res. (2009) (8)8:3808-3815.
Cutillas et al., "Biological Signalling Activity Measurements Using Mass Spectrometry", Biochem. J. (2011) 434:189-199.

* cited by examiner

SEQUENCE LISTING

<160> NUMBER OF SEQ ID NOS: 28

<210> SEQ ID NO 1
<211> LENGTH: 16
<212> TYPE: PRT
<213> ORGANISM: Homo sapiens
<220> FEATURE:
<221> NAME/KEY: SOURCE
<222> LOCATION: 1..16
<223> OTHER INFORMATION: /mol_type="protein"
      /organism="Homo sapiens"
<220> FEATURE:
<221> NAME/KEY: MOD_RES
<222> LOCATION: 13
<223> OTHER INFORMATION: phosphorylation

<400> SEQUENCE: 1

Leu Ala Asp Phe Gly Val Ala Gly Gln Leu Thr Asp Thr Gln Ile Lys
1               5                   10                  15

<210> SEQ ID NO 2
<211> LENGTH: 15
<212> TYPE: PRT
<213> ORGANISM: Homo sapiens
<220> FEATURE:
<221> NAME/KEY: SOURCE
<222> LOCATION: 1..15
<223> OTHER INFORMATION: /mol_type="protein"
      /organism="Homo sapiens"

<400> SEQUENCE: 2

Arg Pro His Phe Pro Gln Phe Ser Tyr Ser Ala Ser Gly Thr Ala
1               5                   10                  15

<210> SEQ ID NO 3
<211> LENGTH: 21
<212> TYPE: PRT
<213> ORGANISM: Homo sapiens
<220> FEATURE:
<221> NAME/KEY: SOURCE
<222> LOCATION: 1..21
<223> OTHER INFORMATION: /mol_type="protein"
      /organism="Homo sapiens"

<400> SEQUENCE: 3

Ser Gly Ser Pro Ser Asp Asn Ser Gly Ala Glu Glu Met Glu Val Ser
1               5                   10                  15

Leu Ala Lys Pro Lys
            20

<210> SEQ ID NO 4
<211> LENGTH: 15
<212> TYPE: PRT
<213> ORGANISM: Homo sapiens
<220> FEATURE:
<221> NAME/KEY: SOURCE
<222> LOCATION: 1..15
<223> OTHER INFORMATION: /mol_type="protein"
      /organism="Homo sapiens"
<220> FEATURE:
<221> NAME/KEY: MOD_RES
<222> LOCATION: 10
<223> OTHER INFORMATION: phosphorylation

<400> SEQUENCE: 4

Gln Val Ala Glu Gln Gly Gly Asp Leu Ser Pro Ala Ala Asn Arg
1               5                   10                  15

<210> SEQ ID NO 5

```
<211> LENGTH: 22
<212> TYPE: PRT
<213> ORGANISM: Homo sapiens
<220> FEATURE:
<221> NAME/KEY: SOURCE
<222> LOCATION: 1..22
<223> OTHER INFORMATION: /mol_type="protein"
      /organism="Homo sapiens"

<400> SEQUENCE: 5

Leu Thr Gln Thr Ser Ser Thr Glu Gln Leu Asn Val Leu Glu Thr Glu
1               5                   10                  15

Thr Glu Val Leu Asn Lys
            20

<210> SEQ ID NO 6
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: phosphorylation

<400> SEQUENCE: 6

Asn Leu Gly Ser Ile Asn Thr Glu Leu Gln Asp Val Gln Arg
1               5                   10

<210> SEQ ID NO 7
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: phosphorylation

<400> SEQUENCE: 7

Asp Met Glu Ser Pro Thr Lys Leu Asp Val Thr Leu Ala Lys
1               5                   10

<210> SEQ ID NO 8
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 8

Gly Thr Tyr Val Pro Ser Ser Pro Thr Arg
1               5                   10

<210> SEQ ID NO 9
<211> LENGTH: 20
<212> TYPE: PRT
<213> ORGANISM: Homo sapiens
<220> FEATURE:
```

```
<221> NAME/KEY: SOURCE
<222> LOCATION: 1..20
<223> OTHER INFORMATION: /mol_type="protein"
      /organism="Homo sapiens"
<220> FEATURE:
<221> NAME/KEY: MOD_RES
<222> LOCATION: 3
<223> OTHER INFORMATION: phosphorylation

<400> SEQUENCE: 9

Lys Leu Ser Gly Asp Gln Ile Thr Leu Pro Thr Thr Val Asp Tyr Ser
1               5                   10                  15

Ser Val Pro Lys
            20

<210> SEQ ID NO 10
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"

<400> SEQUENCE: 10

Ser Ser Ser Val Gly Ser Ser Ser Tyr Pro Ile Ser Pro Ala Val
1               5                   10                  15

Ser Arg

<210> SEQ ID NO 11
<211> LENGTH: 15
<212> TYPE: PRT
<213> ORGANISM: Homo sapiens
<220> FEATURE:
<221> NAME/KEY: SOURCE
<222> LOCATION: 1..15
<223> OTHER INFORMATION: /mol_type="protein"
      /organism="Homo sapiens"

<400> SEQUENCE: 11

Asn Glu Gly Ser Glu Ser Ala Pro Glu Gly Gln Ala Gln Gln Arg
1               5                   10                  15

<210> SEQ ID NO 12
<211> LENGTH: 8
<212> TYPE: PRT
<213> ORGANISM: Homo sapiens
<220> FEATURE:
<221> NAME/KEY: SOURCE
<222> LOCATION: 1..8
<223> OTHER INFORMATION: /mol_type="protein"
      /organism="Homo sapiens"

<400> SEQUENCE: 12

Leu Asn Thr Ser Asp Phe Gln Lys
1               5

<210> SEQ ID NO 13
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"
<220> FEATURE:
<221> NAME/KEY: MOD_RES
```

<222> LOCATION: 3
<223> OTHER INFORMATION: phosphorylation

<400> SEQUENCE: 13

Leu Gly Ser Val Asp Ser Phe Glu Arg
1               5

<210> SEQ ID NO 14
<211> LENGTH: 8
<212> TYPE: PRT
<213> ORGANISM: Homo sapiens
<220> FEATURE:
<221> NAME/KEY: SOURCE
<222> LOCATION: 1..8
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: phosphorylation

<400> SEQUENCE: 14

Leu Asn Ala Ser Pro Ala Ala Arg
1               5

<210> SEQ ID NO 15
<211> LENGTH: 8
<212> TYPE: PRT
<213> ORGANISM: Homo sapiens
<220> FEATURE:
<221> NAME/KEY: SOURCE
<222> LOCATION: 1..8
<223> OTHER INFORMATION: /mol_type="protein"
      /organism="Homo sapiens"
<220> FEATURE:
<221> NAME/KEY: MOD_RES
<222> LOCATION: 3
<223> OTHER INFORMATION: phosphorylation

<400> SEQUENCE: 15

Gln Lys Ser Pro Glu Ile His Arg
1               5

<210> SEQ ID NO 16
<211> LENGTH: 15
<212> TYPE: PRT
<213> ORGANISM: Homo sapiens
<220> FEATURE:
<221> NAME/KEY: SOURCE
<222> LOCATION: 1..15
<223> OTHER INFORMATION: /mol_type="protein"
      /organism="Homo sapiens"

<400> SEQUENCE: 16

Ala Glu Asp Gly Ala Thr Pro Ser Pro Ser Asn Glu Thr Pro Lys
1               5                   10                  15

<210> SEQ ID NO 17
<211> LENGTH: 8
<212> TYPE: PRT
<213> ORGANISM: Homo sapiens
<220> FEATURE:
<221> NAME/KEY: SOURCE
<222> LOCATION: 1..8
<223> OTHER INFORMATION: /mol_type="protein"
      /organism="Homo sapiens"

<400> SEQUENCE: 17

Ile Ser Ala Ser Ser Ala Thr Arg
1               5

```
<210> SEQ ID NO 18
<211> LENGTH: 8
<212> TYPE: PRT
<213> ORGANISM: Homo sapiens
<220> FEATURE:
<221> NAME/KEY: SOURCE
<222> LOCATION: 1..8
<223> OTHER INFORMATION: /mol_type="protein"
      /organism="Homo sapiens"

<400> SEQUENCE: 18

Ser Ser Ser Leu Asp Met Asn Arg
1               5

<210> SEQ ID NO 19
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 19

Val Ser Asn Gly Ser Pro Ser Leu Glu Arg
1               5                   10

<210> SEQ ID NO 20
<211> LENGTH: 20
<212> TYPE: PRT
<213> ORGANISM: Homo sapiens
<220> FEATURE:
<221> NAME/KEY: SOURCE
<222> LOCATION: 1..20
<223> OTHER INFORMATION: /mol_type="protein"
      /organism="Homo sapiens"

<400> SEQUENCE: 20

Gly Asp Gln Pro Ala Ala Ser Gly Asp Ser Asp Asp Asp Glu Pro Pro
1               5                   10                  15

Pro Leu Pro Arg
            20

<210> SEQ ID NO 21
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"

<400> SEQUENCE: 21

Arg Ser Pro Thr Leu Arg
1               5

<210> SEQ ID NO 22
<211> LENGTH: 20
<212> TYPE: PRT
<213> ORGANISM: Homo sapiens
<220> FEATURE:
<221> NAME/KEY: SOURCE
<222> LOCATION: 1..20
<223> OTHER INFORMATION: /mol_type="protein"
      /organism="Homo sapiens"
<220> FEATURE:
```

```
<221> NAME/KEY: MOD_RES
<222> LOCATION: 4
<223> OTHER INFORMATION: phosphorylation

<400> SEQUENCE: 22

Val Gly Asp Ser Gln Asn Pro Leu Leu Ser Asp Gly Asp Leu Ser Thr
1               5                   10                  15

Met Ile Gly Lys
            20

<210> SEQ ID NO 23
<211> LENGTH: 8
<212> TYPE: PRT
<213> ORGANISM: Homo sapiens
<220> FEATURE:
<221> NAME/KEY: SOURCE
<222> LOCATION: 1..8
<223> OTHER INFORMATION: /mol_type="protein"
      /organism="Homo sapiens"
<220> FEATURE:
<221> NAME/KEY: MOD_RES
<222> LOCATION: 3
<223> OTHER INFORMATION: phosphorylation

<400> SEQUENCE: 23

Thr Ala Ser Phe Ser Glu Ser Arg
1               5

<210> SEQ ID NO 24
<211> LENGTH: 20
<212> TYPE: PRT
<213> ORGANISM: Homo sapiens
<220> FEATURE:
<221> NAME/KEY: SOURCE
<222> LOCATION: 1..20
<223> OTHER INFORMATION: /mol_type="protein"
      /organism="Homo sapiens"
<220> FEATURE:
<221> NAME/KEY: MOD_RES
<222> LOCATION: 8
<223> OTHER INFORMATION: phosphorylation

<400> SEQUENCE: 24

Thr Ile Gly Gly Gly Asp Asp Ser Phe Asn Thr Phe Phe Ser Glu Thr
1               5                   10                  15

Gly Ala Gly Lys
            20

<210> SEQ ID NO 25
<211> LENGTH: 13
<212> TYPE: PRT
<213> ORGANISM: Homo sapiens
<220> FEATURE:
<221> NAME/KEY: MOD_RES
<222> LOCATION: 2
<223> OTHER INFORMATION: phosphorylation
<220> FEATURE:
<221> NAME/KEY: MOD_RES
<222> LOCATION: 11
<223> OTHER INFORMATION: phosphorylation
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 25

Ala Ser Gly Gln Ala Phe Glu Leu Ile Leu Ser Pro Arg
1               5                   10
```

-continued

```
<210> SEQ ID NO 26
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /organism="Homo sapiens"
<220> FEATURE:
<221> NAME/KEY: MOD_RES
<222> LOCATION: 2
<223> OTHER INFORMATION: phosphorylation

<400> SEQUENCE: 26

Asn Ser Leu Pro Gln Ile Pro Met Leu Asn Leu Glu Ala Arg
1               5                   10

<210> SEQ ID NO 27
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"
<220> FEATURE:
<221> NAME/KEY: MOD_RES
<222> LOCATION: 2
<223> OTHER INFORMATION: phosphorylation

<400> SEQUENCE: 27

Ser Thr Asp Ser Pro Gly Ala Asp Ala Glu Leu Pro Glu Ser Ala Ala
1               5                   10                  15

Arg

<210> SEQ ID NO 28
<211> LENGTH: 6
<212> TYPE: PRT
<213> ORGANISM: Homo sapiens
<220> FEATURE:
<221> NAME/KEY: SOURCE
<222> LOCATION: 1..6
<223> OTHER INFORMATION: /mol_type="protein"
      /organism="Homo sapiens"
<220> FEATURE:
<221> NAME/KEY: MOD_RES
<222> LOCATION: 4
<223> OTHER INFORMATION: phosphorylation

<400> SEQUENCE: 28

Arg Leu Ser Ser Leu Arg
1               5
```

US 9,747,412 B2

METHOD FOR IDENTIFYING ACTIVATION OF TRANSFERASES

FIELD OF THE INVENTION

The present invention relates to a method for identifying differential activation of a bisubstrate protein modifying enzyme between samples and a method for identifying substrates of bisubstrate protein modifying enzymes. Bisubstrate protein modifying enzymes include protein kinases.

BACKGROUND TO THE INVENTION

Kinases or phosphotransferases are enzymes which transfer phosphate groups from high-energy donor molecules such as adenosine triphosphate (ATP) to specific substrates in a process known as phosphorylation. The chemical activity of a protein kinase involves transferring a phosphate group from a nucleoside triphosphate such as ATP and covalently attaching it to one of three amino acids that have a free hydroxyl group. Most protein kinases act on both serine and threonine, others act on tyrosine and some act on all three of these amino acids. There are also protein kinases that phosphorylate other amino acids, including histidine.

Protein kinases play a fundamental role in signal transduction and thus are key mediators of essential cellular processes such as metabolism, growth, cell cycle progression, migration and apoptosis. Disruption of signalling pathways is associated with the pathology of many diseases, including cancer, and thus understanding the activity of the enzymes that control transduction is of great interest clue to their potential as therapeutic targets and biomarkers.

Protein phosphorylation is a reflection of kinase activity and current mass spectrometry (MS) based phosphoproteomic analysis provides the unprecedented opportunity to evaluate the activity of multiple signalling pathways in a single assay. However, such global approaches are not yet possible because in most cases we do not yet know the identity of the kinases acting on the sites that we can measure using phosphoproteomic techniques. Furthermore, there are more than 500 kinase genes in the human genome and despite intense research, methods for global and unbiased analysis of kinase activities have not yet been reported.

SUMMARY OF THE INVENTION

The present inventors have devised a technique to quantify the activity of bisubstrate protein modifying enzymes such as protein kinases in a global fashion and without a preconception of the enzymes that may be active in the cell or tissue under investigation.

Accordingly, in a first aspect, the present invention provides a method for identifying differential activation of a bisubstrate protein modifying enzyme between samples, comprising:
  exposing a first sample to x different concentrations of the non-protein substrate of said enzyme, wherein x is 2 or greater than 2;
  (ii) quantifying modification of a polypeptide in said sample at each of the x different concentrations of the non-protein substrate;
  (iii) determining the affinity of said enzyme for said non-protein substrate;
  (iv) repeating steps (i) to (iii) for a second or subsequent sample; and
  (v) comparing the affinity of said enzyme for said non-protein substrate between said samples;
wherein a difference in affinity of said enzyme for said non-protein substrate between samples is indicative of differential activation of said enzyme between samples.

DETAILED DESCRIPTION OF THE INVENTION

The method of the first aspect of the invention is a method for identifying differential activation of a bisubstrate protein modifying enzyme between samples. The method involves quantifying modification of a polypeptide in a first sample at different concentrations of a non-protein substrate of a bisubstrate protein modifying enzyme. Changing the concentration of the non-protein substrate allows the calculation of the affinity of the enzyme for each modification. A difference in affinity constants between samples indicates differential activation or activity of enzymes between samples. The method of the first aspect of the invention is an in vitro method.

By "bisubstrate protein modifying enzyme" is meant an enzyme that has two substrates, one of which is a protein. The other substrate, referred to herein as the non-protein substrate, is a molecule having a group that is transferred from the non-protein substrate to the protein substrate in the reaction catalysed by the enzyme. Such enzymes can also be referred to as protein transferases. A transferase is an enzyme that catalyses the transfer of a functional group from one molecule (often called the donor) to another (often called the acceptor). Thus a protein transferase is an enzyme that catalyses the transfer of a functional group from a donor to an acceptor which is a protein. It can therefore be seen for bisubstrate protein modifying enzymes, the non-protein substrate is the donor and a protein (or part of a protein such as a polypeptide or peptide) is the acceptor.

Examples of bisubstrate protein modifying enzymes include protein kinases, whose non-protein substrate is ATP and which transfer phosphate groups from the ATP onto a protein substrate in a process known as phosphorylation. Other examples include protein acetyltransferases, whose non-protein substrate is a compound having an acetyl group, such as acetyl coenzyme A (acetyl CoA); protein glycosyltransferases, whose non-protein substrate is an activated nucleotide sugar (also known as the "glycosyl donor"); protein methyltransferases, whose non-protein substrate is a compound having a methyl group; and protein palmitoyltransferases, whose non-protein substrate is a compound containing the lipid palmitoyl, such as palmitoyl CoA.

In one embodiment, the bisubstrate protein modifying enzyme is a protein kinase. In this embodiment, the method of the first aspect of the invention is a method for identifying differential activation of a protein kinase between samples, comprising:
  (i) incubating a first sample with x different concentrations of ATP, wherein x is 2 or greater than 2;
  (ii) quantifying phosphorylation of a polypeptide in said sample at each of the x different concentrations of ATP;
  (iii) determining the affinity of said protein kinase for ATP;
  (iv) repeating steps (i) to (iii) for a second or subsequent sample; and
  (v) comparing the affinity of said protein kinase for ATP between said samples;
wherein a difference in affinity of said protein kinase for ATP between samples is indicative of differential activation of a protein kinase between samples.

Step (i) of the method of the first aspect of the invention involves exposing a first sample to x different concentrations of the non-protein substrate of said enzyme, wherein x is 2 or greater than 2. This step is subsequently repeated for a second or subsequent sample.

The samples (first, second and/or subsequent) used in the method of the first aspect of the invention can be any samples which contain peptides. The samples are typically biological samples and can thus be any type of sample obtained from a biological source, for example a sample obtained from a human, animal, plant or bacterium. The invention thus encompasses the use of samples obtained from human and non-human sources.

The samples used in the method of the first aspect of the present invention can be from any species of interest. Typically, the samples are from a human or animal. The animal is typically a mammal, for example a rodent such as a mouse, rat or guinea pig, or an ungulate such as a cow, sheep or goat. The animal is alternatively a bird, such as a chicken, a fish, such as a zebra fish, a nematode, such as the worm *Caenorhabditis elegans*, or an insect, such as the fruit fly *Drosophila melanogaster*. The samples used in the method of the first aspect of the invention can also be from other life-forms such as bacteria and yeast. The samples used in the method of the first aspect of the invention are typically samples from an experimentally important species of bacterium such as *Escherichia coli, Salmonella enterica, Streptococcus pneumoniae* or *Staphylococcus aureus*, or of yeast such as the baker's yeast *Saccharomyces cerevisiae* or the fission yeast *Schizosaccharomyces pombe*. The samples used in the method of the first aspect of the invention can alternatively be from a plant or fungus or a virus.

Typically, the biological sample is derived from a human, and can be, for example, a sample of a bodily fluid such as urine or blood, or another tissue. Typically, the biological sample is a cell line or a tissue, typically a primary tissue. For example, the sample can be a tissue from a human or animal. The human or animal can be healthy or diseased. Alternatively, the sample can be a cell line derived from healthy or diseased human or animal cells.

The sample is typically prepared prior to step (i) of the method of the first aspect of the invention by lysing cells in the sample to produce a cell lysate. The sample (first, second and/or subsequent) used in the method of the first aspect of the invention can therefore be a cell lysate. The term "lysing cells" as used herein has its usual meaning in the art, i.e. splitting open cells. The cells can be lysed using any suitable means known in the art, for example using physical methods such as mechanical lysis (for example using a Waring blender), liquid homogenization, sonication or manual lysis (for example using a pestle and mortar) or detergent-based methods such as CHAPS or Triton-X. Typically, the cells are lysed using a combination of Tris-HCl, Triton and EDTA, optionally supplemented with protease inhibitors and/or phosphatase inhibitors.

The method of the first aspect of the invention is typically used to identify differential activation of a bisubstrate protein modifying enzyme present in a sample such as a cell lysate, for example, an endogenous protein kinase present in a cell lysate. Such bisubstrate protein modifying enzymes act to modify endogenous protein substrates in a sample such as a cell lysate when exposed to the non-protein substrate of the enzyme.

In step (i) of the method of the first aspect of the invention, a first sample is exposed to x different concentrations of the non-protein substrate of said enzyme. This step is subsequently repeated for a second or subsequent sample. This step can be carried out by adding a particular concentration of the non-protein substrate, optionally in a suitable buffer, to the sample, which can be a cell lysate. Typically, the first, second or subsequent sample is incubated with x different concentrations of the non-protein substrate under conditions suitable for the enzyme to act on the non-protein substrate. The first, second or subsequent sample is incubated for a sufficient time and at a suitable temperature, with mixing if necessary. In one specific embodiment, the sample is incubated at 30° C. for 5 minutes, with mixing. The reaction can be stopped, for example, by the addition of urea.

In step (i) of the method of the first aspect of the invention, a first sample is exposed to x different concentrations of the non-protein substrate of said enzyme, wherein x is 2 or greater than 2. Generally speaking, x is at least 3, typically 4 or 5 or even 6, 7, 8, 9 or 10. However, there is no limit on x and therefore the number of different concentrations of the non-protein substrate that can be used, as long as the concentrations of the non-protein substrate can be plotted on a graph and used to calculate the affinity of the enzyme for the non-protein substrate.

Any suitable concentrations of the non-protein substrate can be used in the method of the first aspect of the present invention. Typically, when the bisubstrate protein modifying enzyme is protein kinase, concentrations of ATP for use in the method of the first aspect of the present invention are in the range from 0 to 500 µM, typically from 0 to 100 µM. For example, concentrations of 0, 10 and 100 µM, 0, 100, 200, 300 and 500 µM or 0, 10, 50, 100 and 500 µM ATP can be used.

Step (ii) of the method of the first aspect of the invention involves quantifying modification of a polypeptide in the sample at each of the x different concentrations of the non-protein substrate. Typically, the sample is a cell lysate. In one embodiment, the modification is phosphorylation. In other embodiments, the modification is acetylation, nitration, glycosylation, methylation and/or lipidation.

Prior to carrying out step (ii) of the method of the first aspect of the invention, a mixture of peptides is typically obtained from the sample by digestion.

Peptides are typically obtained from proteins by breaking down longer proteins into shorter peptides. Protein breakdown is also commonly referred to as digestion. Thus, in one embodiment, peptides are obtained from the sample by digestion of proteins in the samples Protein digestion can be carried out in the present invention using any suitable agent known in the art.

Protein digestion is typically carried out using a protease. Any suitable protease can be used in the present invention. In the present invention, the protease is typically trypsin, chymotrypsin, Arg-C, pepsin, V8, Lys-C, Asp-C and/or AspN. Alternatively, the proteins can be cleaved chemically, for example using hydroxylamine, formic acid, cyanogen bromide, BNPS-skatole, 2-nitro-5-thiocyanobenzoic acid (NTCB) or any other suitable agent.

The peptides used in the present invention and which are typically produced by protein cleavage as described above are typically suitable for mass spectrometric analysis. Typically, such peptides are between about 5 and 30 amino acids long, for example from 7 to 25 amino acids, from 10 to 20 amino acids, from 12 to 18 amino acids or from 14 to 16 amino acids. However, shorter and longer peptides, such as between about 2 and about 50, for example from about 3 to about 40 or from about 4 to about 45 amino acids can also be used. The length of the peptide that can be analysed is limited by the ability of the mass spectrometer to sequence such long peptides. In certain cases polypeptides of up to 300 amino acids can be analysed.

In one embodiment, the polypeptide that is quantified in step (ii) is purified prior to step (ii). Purification can be carried out using any technique described herein in detail in relation to the second aspect of the invention. Such techniques are applicable in their entirety to the first aspect of the invention.

Quantification of modifications such as phosphorylation can be carried out using any suitable method. Typically, quantification can be carried out by any method involving mass spectrometry (MS), such as liquid chromatography-mass spectrometry (LC-MS). The LC-MS or LC-MS/MS is typically label-free MS.

In the method of the first aspect of the present invention, quantification of phosphorylation is typically carried out using the TIQUAS (targeted and in-depth quantification of signalling) technique, as described in WO 2010/119261 (International patent application no. PCT/GB2010/000770) and incorporated herein in its entirety by reference. This technique allows for sensitive, rapid and comprehensive quantification of signalling pathway activity. The method can, in one simple assay, simultaneously measure the amounts of thousands of phosphorylation sites on proteins. As set out in WO 2010/119261, the TIQUAS technique can also be used to quantify modified peptides other than phosphorylated peptides. In fact, the TIQUAS technique can be used to quantify peptides which contain any modifications which can be detected by mass spectrometry.

In this embodiment of the method of the first aspect of the invention, step (ii) is carried out using a method comprising the following steps:
    (a) adding reference modified peptides to the peptides obtained in step (i) to produce a mixture of peptides and reference modified peptides;
    (b) carrying out mass spectrometry (MS) on said mixture of peptides and reference modified peptides to obtain data relating to the peptides in the sample; and
    (c) comparing the data relating to the peptides in the sample with data in a database of modified peptides using a computer programme;
wherein the database of modified peptides is compiled by a method comprising:
    i. obtaining peptides from a sample;
    ii. enriching modified peptides from the peptides obtained in step i;
    iii. carrying out liquid chromatography-tandem mass spectrometry (LC-MS/MS) on the enriched modified peptides obtained in step ii;
    iv. comparing the modified peptides detected in step iii to a known reference database in order to identify the modified peptides; and
    v. compiling data relating to the modified peptides identified in step iv into a database.

The TIQUAS technique is described herein in detail in relation to the second aspect of the invention and is applicable in its entirety to the first aspect of the invention.

As an alternative to using the TIQUAS technique, in the method of the first aspect of the invention, quantification of modifications such as phosphorylation can also be carried out using MS techniques that use isotope labels for quantification, such as metabolic labeling (e.g., stable isotope labeled amino acids in culture, (SILAC); Olsen, J. V. et al. *Cell* 127, 635-648 (2006)), and chemical derivatization (e.g., iTRAQ (Ross, P. L.; et al. *Mol Cell Proteomics* 2004, 3, (12), 1154-69), ICAT (Gygi, S. P. et al. *Nat Biotechnol* 17, 994-999 (1999)), TMT (Dayon L et al, Anal Chem. 2008 Apr. 15; 80(8):2921-31) techniques. In the method of the invention, modifications such as phosphorylation can be quantified with LC-MS techniques that measure the intensities of the unfragmented ions or with LC-MS/MS techniques that measure the intensities of fragment ions (such as Selected Reaction Monitoring (SRM), also named multiple reaction monitoring (MRM)).

Step (iii) of the method of the first aspect of the invention comprises determining the affinity of the enzyme (such as a protein kinase) for the non-protein substrate.

Figure 2A:
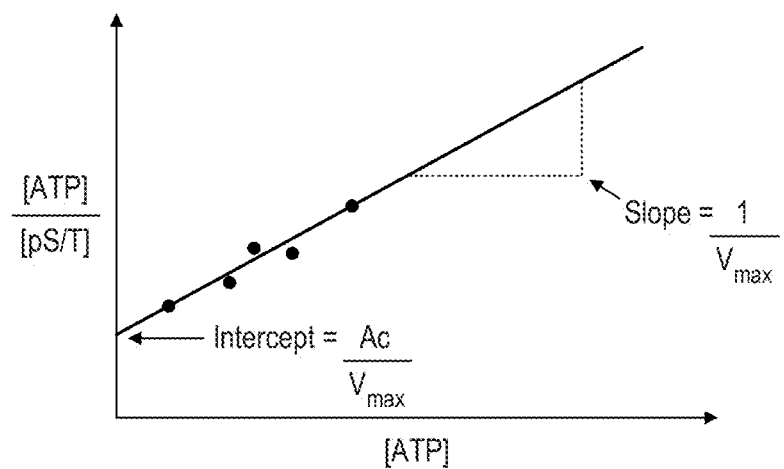
Figure 2B:
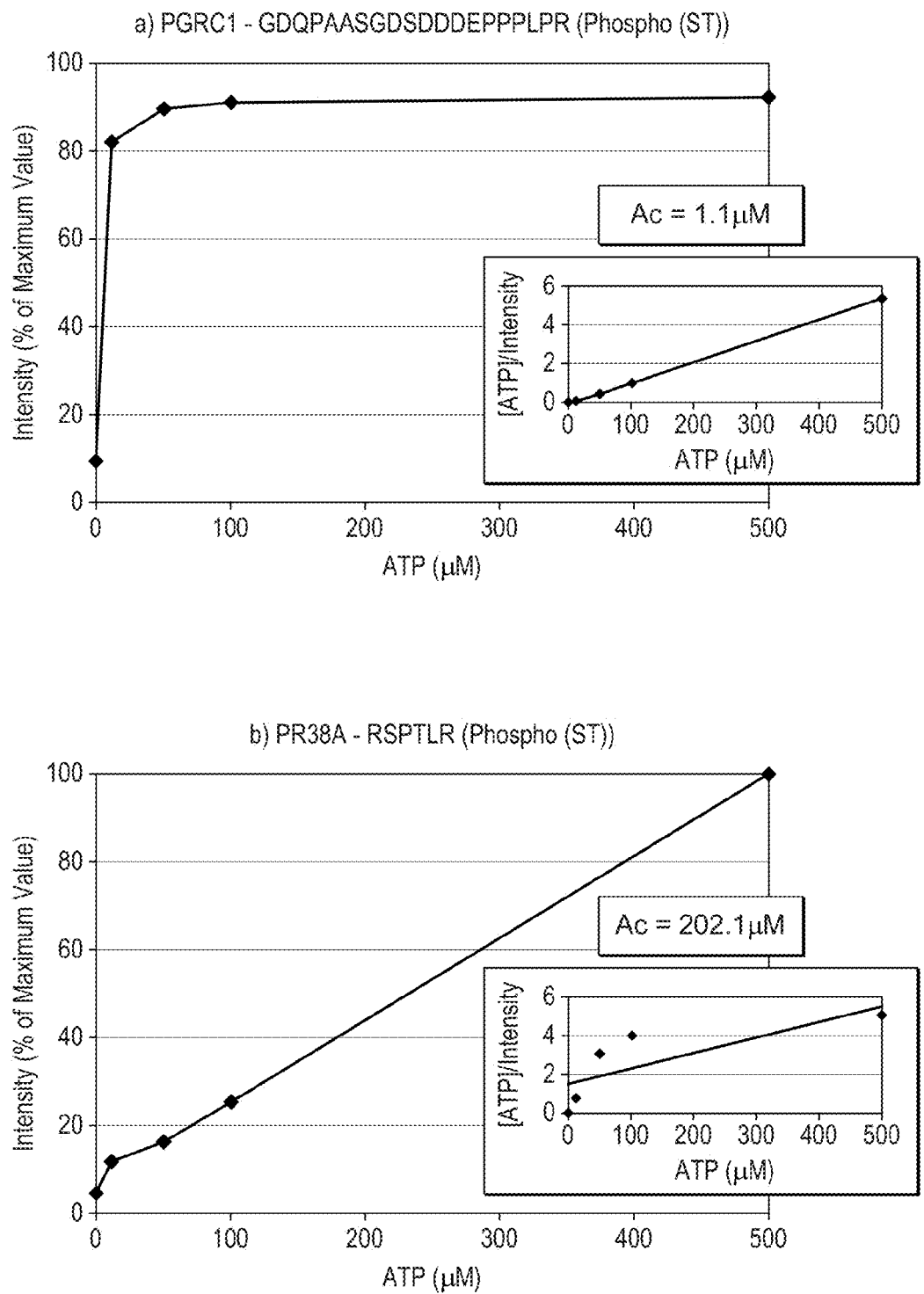

The affinity of the enzyme (for example a protein kinase) for the non-protein substrate, for example ATP, can be determined using the principles of Michaelis-Menten kinetics. For example, an affinity constant (Ac, related to Km) can be calculated for each peptide, as shown in FIG. 2A. FIG. 2B shows two representative responses; a) a protein kinase activity with high affinity for ATP (low Ac) and b) a protein kinase activity with low affinity for ATP (high Ac).

In one embodiment, step (iii) of the method of the first aspect of the invention comprises:
    (a) determining whether modification of the peptide is increased when the concentration of the non-protein substrate is increased; and, if modification of the peptide is increased when the concentration of the non-protein substrate is increased;
    (b) calculating the affinity constant (Ac) of the enzyme for the non-protein substrate.

In this embodiment, when the enzyme is a protein kinase, step (iii) comprises:
    (a) determining whether phosphorylation of the peptide is increased when the concentration of the non-protein substrate is increased; and, if phosphorylation of the peptide is increased when the concentration of the non-protein substrate is increased;
    (b) calculating the affinity constant (Ac) of the protein kinase for the non-protein substrate.

Step (iv) of the method of the first aspect of the invention comprises repeating steps (i) to (iii) for a second or subsequent sample.

Step (v) of the method of the first aspect of the invention then comprises comparing the affinity of the enzyme for the non-protein substrate between the samples.

The measurement of the Ac allows the comparison of the affinity of the enzyme for the non-protein substrate between samples according to the affinity of enzyme (such as protein kinase) reactions to said substrate. A difference in affinity constants between samples indicates differential activation or activity of the enzyme between samples.

In one embodiment, the method of the first aspect of the invention involves quantification of the activity of endogenous kinases from a sample in phosphorylating endogenous proteins in the sample. Quantification can be carried out using any of the methods described herein but is typically carried out using the TIQUAS method described herein. Changing the concentration of ATP allows the calculation of the affinity of the protein kinase for each phosphorylation. A difference in affinity constants between samples indicates differential activation or activity of endogenous kinases between samples. This method can be used, for example, to detect differences in the activity of endogenous kinases in samples from diseased and normal cells or tissues, or in samples treated with drugs such as enzyme inhibitors or activators.

The present inventors have devised a technique to quantify the activity of bisubstrate protein modifying enzymes such as protein kinases in a global fashion and without a preconception of the enzymes that may be active in the cell or tissue under investigation. In this technique, which is termed Global Kinase Activity Profiling (GKAP), protein kinases present in cell lysates phosphorylate endogenous substrates also present in the lysate under defined conditions. Reaction products are then quantified using standard phosphoproteomics techniques based on LC-MS/MS. Several hundred kinase reactions could be quantified with this approach, >300 of which increased as a function of a physiological stimulus (treatment with EGF), while others decreased by treatment with the kinase inhibitors LY292004 or U0126. GKAP also detected marked differences in the patterns of kinase activities in leukemia cell lines exhibiting different sensitivity to treatment with kinase inhibitors. These results reveal that GKAP detects kinase activities modulated by growth factors and by pharmacological inhibitors, and that these activities correlate with cell phenotypes and drug responses. The present inventors have thus demonstrated an approach for global and unbiased analysis of kinase activities for the first time.

The present inventors have also devised a method for identifying substrates of bisubstrate protein modifying enzymes such as protein kinases. The method can be used to identify in vivo substrates of bisubstrate protein modifying enzymes such as protein kinases. By "in vivo substrates of bisubstrate protein modifying enzymes" is meant a protein, polypeptide or peptide substrate of such an enzyme which is a substrate in vivo.

Accordingly, in a second aspect, the present invention provides a method for identifying an in vivo substrate of a bisubstrate protein modifying enzyme, comprising:

(i) exposing a bisubstrate protein modifying enzyme to x different concentrations of a first substrate, wherein x is 2 or greater than 2, while leaving the concentration of a second substrate constant, wherein one of the first and second substrates is the non-protein substrate of said enzyme and the other is a mixture of polypeptides;

(ii) quantifying modification of a polypeptide in said mixture of polypeptides at each of the x different concentrations of said first substrate; and (iii) determining the affinity of said enzyme for said first substrate;

wherein a high affinity of said enzyme for said first substrate is indicative of said polypeptide being an in vivo substrate of said enzyme.

The method of the second aspect of the present invention is a method for identifying an in vivo substrate of a bisubstrate protein modifying enzyme such as a protein kinase. The present invention therefore allows the identification of which in vitro substrates of a bisubstrate protein modifying enzyme such as a protein kinase will also be in vivo substrates. The method of the second aspect of the invention is an in vitro method.

In one embodiment, the bisubstrate protein modifying enzyme is a protein kinase. In this embodiment, the method of the second aspect of the present invention is a method for identifying an in vivo substrate of a protein kinase, comprising:

(i) exposing a protein kinase to x different concentrations of a first substrate, wherein x is 2 or greater than 2, while leaving the concentration of a second substrate constant, wherein one of the first and second substrates is ATP and the other is a mixture of polypeptides;

(ii) quantifying phosphorylation of a polypeptide in said mixture of polypeptides at each of the x different concentrations of said first substrate; and (iii) determining the affinity of said protein kinase for said first substrate;

wherein a high affinity of said protein kinase for said first substrate is indicative of said polypeptide being an in vivo substrate of said protein kinase.

Step (i) of the method of the second aspect of the invention comprises exposing a bisubstrate protein modifying enzyme such as a protein kinase to x different concentrations of a first substrate, wherein x is 2 or greater than 2, while leaving the concentration of a second substrate constant, wherein one of the first and second substrates is the non-protein substrate of said enzyme (for example ATP for a protein kinase) and the other is a mixture of polypeptides. As set out above, by "bisubstrate protein modifying enzyme" is meant an enzyme that has two substrates, one of which is a protein. For example, protein kinases have two substrates, the protein that is phosphorylated and ATP. The methods of the present invention utilise this feature of bisubstrate protein modifying enzymes such as protein kinases.

Step (i) of the method of the second aspect of the invention comprises exposing a bisubstrate protein modifying enzyme to x different concentrations of a first substrate, wherein x is 2 or greater than 2, while leaving the concentration of a second substrate constant. Typically, the bisubstrate protein modifying enzyme is incubated with x different concentrations of the first substrate for a sufficient time for the enzyme to act on the first substrate.

In one embodiment, the first substrate is the non-protein substrate of the enzyme and the other is a mixture of polypeptides. In this embodiment, when the bisubstrate protein modifying enzyme is a protein kinase the first substrate is ATP and second substrate is a mixture of polypeptides.

In another embodiment, the first substrate is a mixture of polypeptides and the second substrate is the non-protein substrate of the enzyme. In this embodiment, when the bisubstrate protein modifying enzyme is a protein kinase the first substrate is a mixture of polypeptides and the second substrate is ATP.

The mixture of polypeptides used in the method of the second aspect of the invention can either be a mixture of undigested proteins or a mixture of peptides that have been obtained by digestion of proteins. The word "polypeptide" used herein thus encompasses both proteins and peptides, depending on the context.

The mixture of polypeptides used in the method of the second aspect of the invention is typically obtained from a sample. Samples used in the method of the second aspect of the invention can be any samples which contain peptides. The samples are typically biological samples and can thus be any type of sample obtained from a biological source, for example a sample obtained from a human, animal, plant or bacterium. The invention thus encompasses the use of samples obtained from human and non-human sources.

The samples used in the method of the present invention can be from any species of interest, as defined in relation to the first aspect of the invention.

Typically, the biological sample is derived from a human, and can be, for example, a sample of a bodily fluid such as urine or blood, or another tissue. Typically, the biological sample is a cell line or a tissue, typically a primary tissue. For example, the sample can be a tissue from a human or animal. The human or animal can be healthy or diseased. Alternatively, the sample can be a cell line derived from healthy or diseased human or animal cells.

When the mixture of polypeptides used in the method of the second aspect of the invention is a mixture of undigested proteins, the mixture of undigested proteins is typically obtained from the sample by lysing cells in the sample to produce a cell lysate. The term "lysing cells" as used herein has its usual meaning in the art, i.e. splitting open cells. The cells can be lysed using any suitable means known in the art, for example using physical methods such as mechanical lysis (for example using a Waring blender), liquid homogenization, sonication or manual lysis (for example using a pestle and mortar) or detergent-based methods such as CHAPS or Triton-X. Typically, the cells are lysed using a combination of Tris-HCl, Triton and EDTA.

The cell lysate is typically depleted of small molecules prior to carrying out step (i). In other words, the proteins are separated from the other components of the lysed cells. This can be done by any suitable means, for example size exclusion filtration.

In one embodiment, typically when the bisubstrate protein modifying enzyme is a protein kinase, the protein (for example the protein in the cell lysate) is dephosphorylated prior to carrying out step (i). This can be carried out in addition or alternatively to depleting the cell lysate of small molecules. Dephosphorylation can be done by any suitable means. In one embodiment, proteins from lysed cells are dephosphorylated by incubating the cell lysate for a suitable period of time to allow endogenous phosphatases to act on the proteins. Alternatively, exogenous phosphatases can be added to the proteins to effect dephosphorylation. Phosphatases suitable for use in this embodiment include tyrosine-specific phosphatases such as PTP1B, serine/threonine specific phosphatases such as PP2c (PPP2CA), histidine phosphatases such as PHP, dual specificity phosphatases such as VHR and DUSP1 to DUSP28 and alkaline phosphatases.

Typically, when the mixture of polypeptides used in the method of the second aspect of the invention is a mixture of undigested proteins, a mixture of peptides is obtained from said mixture of undigested proteins prior to step (ii). In this embodiment, the method of the second aspect of the invention comprises the following steps:
  (i) exposing a bisubstrate protein modifying enzyme to x different concentrations of a first substrate, wherein x is 2 or greater than 2, while leaving the concentration of a second substrate constant, wherein one of the first and second substrates is the non-protein substrate of said enzyme and the other is a mixture of polypeptides, wherein the mixture of polypeptides is a mixture of undigested proteins; and obtaining a mixture of peptides from said mixture of undigested proteins;
  (ii) quantifying modification of a peptide in said mixture of peptides at each of the x different concentrations of said first substrate; and
  (iii) determining the affinity of said enzyme for said first substrate;
  wherein a high affinity of said enzyme for said first substrate is indicative of said peptide being an in vivo substrate of said enzyme.

In this embodiment, where the bisubstrate protein modifying enzyme is a protein kinase, the method of the second aspect of the invention comprises the following steps:
  (i) exposing a protein kinase to x different concentrations of a first substrate, wherein x is 2 or greater than 2, while leaving the concentration of a second substrate constant, wherein one of the first and second substrates is ATP and the other is a mixture of polypeptides, wherein the mixture of polypeptides is a mixture of undigested proteins; and obtaining a mixture of peptides from said mixture of undigested proteins;
  (ii) quantifying phosphorylation of a peptide in said mixture of peptides at each of the x different concentrations of said first substrate; and
  (iii) determining the affinity of said protein kinase for said first substrate;
  wherein a high affinity of said protein kinase for said first substrate is indicative of said peptide being an in vivo substrate of said protein kinase.

In an alternative embodiment, the mixture of polypeptides used in the method of the second aspect of the invention is a mixture of peptides that have been obtained by digestion of proteins. In this embodiment, the method of the second aspect of the invention comprises the following steps:
  (i) obtaining a mixture of peptides by digestion of proteins; and exposing a bisubstrate protein modifying enzyme to x different concentrations of a first substrate, wherein x is 2 or greater than 2, while leaving the concentration of a second substrate constant, wherein one of the first and second substrates is the non-protein substrate of said enzyme and the other is a mixture of peptides;
  (ii) quantifying modification of a peptide in said mixture of peptides at each of the x different concentrations of said first substrate; and
  (iii) determining the affinity of said enzyme for said first substrate;
  wherein a high affinity of said enzyme for said first substrate is indicative of said peptide being an in vivo substrate of said enzyme.

In one embodiment, where the bisubstrate protein modifying enzyme is a protein kinase, the method of the second aspect of the invention comprises the following steps:
  (i) obtaining a mixture of peptides by digestion of proteins; and exposing a protein kinase to x different concentrations of a first substrate, wherein x is 2 or greater than 2, while leaving the concentration of a second substrate constant, wherein one of the first and second substrates is ATP and the other is a mixture of peptides;
  (ii) quantifying phosphorylation of a peptide in said mixture of peptides at each of the x different concentrations of said first substrate; and
  (iii) determining the affinity of said protein kinase for said first substrate;
  wherein a high affinity of said protein kinase for said first substrate is indicative of said peptide being an in vivo substrate of said protein kinase.

It can therefore be seen that in both of these embodiments, step (i) of the method of the second aspect of the invention results in a mixture of peptides that have been exposed to a bisubstrate protein modifying enzyme such as a protein kinase.

In both of these embodiments, a mixture of peptides is obtained from a mixture of undigested proteins. Peptides are typically obtained from proteins by breaking down longer proteins into shorter peptides. Protein breakdown is also commonly referred to as digestion. Thus, in one embodiment, peptides are obtained from the samples by digestion of proteins in the samples. Protein digestion can be carried out in the present invention using any suitable agent known in the art.

Protein digestion is typically carried out using a protease. Any suitable protease can be used in the present invention. In the present invention, the protease is typically trypsin, chymotrypsin, Arg-C, pepsin, V8, Lys-C, Asp-C and/or AspN. Alternatively, the proteins can be cleaved chemically, for example using hydroxylamine, formic acid, cyanogen bromide, BNPS-skatole, 2-nitro-5-thiocyanobenzoic acid (NTCB) or any other suitable agent.

The peptides used in the present invention and which are typically produced by protein cleavage as described above are typically suitable for mass spectrometric analysis. Typically, such peptides are between about 5 and 30 amino acids long, for example from 7 to 25 amino acids, from 10 to 20 amino acids, from 12 to 18 amino acids or from 14 to 16 amino acids. However, shorter and longer peptides, such as between about 2 and about 50, for example from about 3 to about 40 or from about 4 to about 45 amino acids can also be used. The length of the peptide that can be analysed is limited by the ability of the mass spectrometer to sequence such long peptides. In certain cases polypeptides of up to 300 amino acids can be analysed.

The term "phosphoprotein" is used herein to refer to a phosphorylated protein and the term "phosphopeptide" is used herein to refer to a phosphorylated peptide. The term "phosphosite" is used herein to mean the site of phosphorylation, for example on a phosphorylated protein or peptide. The term "phosphoproteomics" is used herein to mean the study of phosphorylated proteins and in particular the identification, characterization and cataloguing of such proteins.

In one embodiment, the peptide or polypeptide that is quantified in step (ii) is purified prior to step (ii). The peptide or polypeptide is typically purified using chromatography.

Typically, the chromatography is immobilized metal ion affinity chromatography (IMAC), for example the adapted IMAC enrichment protocol described in Alcolea, M. P. et al., *J Proteome Res* 8 (8), 3808 (2009). Other types of chromatography can alternatively be used, such as titanium dioxide ($TiO_2$) chromatography, and/or zirconium dioxide ($ZrO_2$) chromatography (Alcolea M P, Cutillas P R. *Methods Mol. Biol.* 658: 111-26 (2010)).

Alternatively, the peptide or polypeptide can be purified using antibody-based methods. In one embodiment of the invention, when the peptide or polypeptide being quantified is a phosphorylated peptide or polypeptide, antibodies with affinity to phosphorylated amino acids such as tyrosine, threonine, serine or histidine are linked (immobilised) to a solid matrix. Phosphorylated peptides are enriched by the ability of these antibodies to specifically bind phosphorylated peptides. Non-phosphorylated peptides are then washed away while phosphorylated peptides are retained on the antibody coated matrices. Elution of phosphorylated peptides from the immobilised antibody is typically carried out using low pH solvents or by any other suitable method that denatures the interaction between antibody and phosphorylated peptides.

In another embodiment of the invention, when the peptides being quantified are acetylated peptides, acetylated peptides are enriched by the use of specific antibodies against acetylated amino acid residues. Such antibodies are linked to a solid matrix and then enriched by the ability of the antibodies to specifically bind acetylated amino acid residues. Non-acetylated peptides are then washed away while acetylated peptides are retained on the immobilised antibody.

As set out above, step (i) of the method of the second aspect of the invention comprises exposing a bisubstrate protein modifying enzyme such as a protein kinase to x different concentrations of a first substrate, wherein x is 2 or greater than 2, while leaving the concentration of a second substrate constant, wherein one of the first and second substrates is the non-protein substrate of said enzyme (for example ATP for a protein kinase) and the other is a mixture of polypeptides.

Examples of bisubstrate protein modifying enzymes include protein kinases, whose non-protein substrate is ATP and which transfer phosphate groups from the ATP onto a protein substrate in a process known as phosphorylation. Other examples include protein acetyltransferases, whose non-protein substrate is a compound having an acetyl group, such as acetyl coenzyme A (acetyl CoA); protein glycosyltransferases, whose non-protein substrate is an activated nucleotide sugar (also known as the "glycosyl donor"); protein methyltransferases, whose non-protein substrate is a compound having a methyl group; and protein palmitoyltransferases, whose non-protein substrate is a compound containing the lipid palmitoyl, such as palmitoyl CoA.

In one embodiment, the bisubstrate protein modifying enzyme is a protein kinase. The protein kinase is typically a recombinant protein kinase. The method of the second aspect of the invention can be used to identify in vivo substrates for any protein kinase. The method of the second aspect of the invention is therefore not limited to the use of any particular protein kinase and can thus be carried out using any protein kinase, for example any protein kinase present in the cell lysate.

Human protein kinases can be divided into a number of groups including AGC kinases, for example protein kinase A (PKA), protein kinase B (PKB) (also known as Akt), protein kinase C (PKC) and protein kinase G (PKG); tyrosine kinases; tyrosine-kinase like kinases; calcium/calmodulin-dependent protein kinases; the casein kinase 1 group; CMGC group, for example CDK, MAPK, GSK3 and CLK kinases; and STE, the homologues of yeast Sterile 7, Sterile 11, and Sterile 20 kinases. For example, the protein kinase used in the method of the invention can be Akt1 which is also known as protein kinase B (PKB).

The reaction of the mixture of polypeptides with the protein kinase in the presence of ATP can be stopped, for example, by the addition of urea.

In the method of the second aspect of the invention, a bisubstrate protein modifying enzyme such as a protein kinase is exposed to x different concentrations of a first substrate, wherein x is 2 or greater than 2, while leaving the concentration of a second substrate constant, wherein one of the first and second substrates is the non-protein substrate of said enzyme (for example ATP for a protein kinase) and the other is a mixture of polypeptides. The enzyme (for example a protein kinase) is therefore exposed to x different concentrations of the non-protein substrate of said enzyme (for example ATP for a protein kinase) or a mixture of polypeptides, wherein x is 2 or greater than 2. Generally speaking, x is at least 3, typically 4 or 5 or even 6, 7, 8, 9 or 10. However, there is no limit on x and therefore the number of different concentrations of the first substrate that can be used, as long as the concentrations of the first substrate can be plotted on a graph and used to calculate the affinity of the protein kinase for the first substrate.

Any suitable concentrations of first and second substrates can be used in the method of the second aspect of the present invention. Typically, concentrations of ATP for use in the present invention when the bisubstrate protein modifying enzyme is a protein kinase are in the range from 0 to 500 µM. For example, concentrations of 0, 10, 50, 100 and 500 µM ATP can be used.

Step (ii) of the method of the second aspect of the invention involves quantifying modification of the peptide or polypeptide at each of the x different concentrations of the first substrate. In one embodiment, the modification is phosphorylation. In other embodiments, the modification is acetylation, nitration, glycosylation, methylation and/or lipidation.

Quantification of modifications such as phosphorylation can be carried out using any suitable method. Typically, quantification can be carried out by any method involving mass spectrometry (MS), such as liquid chromatography-mass spectrometry (LC-MS). The LC-MS or LC-MS/MS is typically label-free MS.

In the methods of the present invention, quantification of phosphorylation is typically carried out using the TIQUAS (targeted and in-depth quantification of signalling) technique, as described in WO 2010/119261 (International patent application no. PCT/GB2010/000770) and incorporated herein in its entirety by reference. This technique allows for sensitive, rapid and comprehensive quantification of signalling pathway activity. The method can, in one simple assay, simultaneously measure the amounts of thousands of phosphorylation sites on proteins. As set out in WO 2010/119261, the TIQUAS technique can also be used to quantify modified peptides other than phosphorylated peptides. In fact, the TIQUAS technique can be used to quantify peptides which contain any modifications which can be detected by mass spectrometry.

In this embodiment of the method of the second aspect of the invention, step (ii) is carried out using a method comprising the following steps:
(a) adding reference modified peptides to the peptides obtained in step (i) to produce a mixture of peptides and reference modified peptides;
(b) carrying out mass spectrometry (MS) on said mixture of peptides and reference modified peptides to obtain data relating to the peptides in the sample; and
(c) comparing the data relating to the peptides in the sample with data in a database of modified peptides using a computer programme;
wherein the database of modified peptides is compiled by a method comprising:
i obtaining peptides from a sample;
ii enriching modified peptides from the peptides obtained in step i;
iii carrying out liquid chromatography-tandem mass spectrometry (LC-MS/MS) on the enriched modified peptides obtained in step ii;
iv comparing the modified peptides detected in step iii to a known reference database in order to identify the modified peptides; and
v compiling data relating to the modified peptides identified in step iv into a database.

In one embodiment of the method of the invention, where the bisubstrate protein modifying enzyme is a protein kinase and the modification is phosphorylation, step (ii) is carried out using a method comprising the following steps:
(a) adding reference phosphorylated peptides to the peptides obtained in step (i) to produce a mixture of peptides and reference phosphorylated peptides;
(b) carrying out mass spectrometry (MS) on said mixture of peptides and reference phosphorylated peptides to obtain data relating to the peptides in the sample; and
(c) comparing the data relating to the peptides in the sample with data in a database of phosphorylated peptides using a computer programme;
wherein the database of phosphorylated peptides is compiled by a method comprising:
i obtaining peptides from a sample;
ii enriching phosphorylated peptides from the peptides obtained in step i;
iii carrying out liquid chromatography-tandem mass spectrometry (LC-MS/MS) on the enriched phosphorylated peptides obtained in step ii;
iv comparing the phosphorylated peptides detected in step iii to a known reference database in order to identify the phosphorylated peptides; and
v compiling data relating to the phosphorylated peptides identified in step iv into a database.

In relation to this embodiment of the invention, the work "peptide" is used interchangeably with the word "polypeptide".

In step (a) of this embodiment, reference modified peptides (typically reference phosphorylated peptides) are added to the peptides obtained in step (i) to produce a mixture of peptides and reference modified peptides (typically reference phosphorylated peptides). Step (a) thus results in one mixture of peptides (including modified ones, typically phosphorylated ones) per sample. The reference modified peptides (typically reference phosphorylated peptides) are also referred to herein as "internal standards" (ISs). Typically, 5 to 10, for example 6 to 9 or 7 to 8, reference modified peptides (typically reference phosphorylated peptides) are added.

In the present invention, the reference modified peptides are typically reference phosphorylated peptides and are typically derived from a reference protein of defined nature and concentration, often referred to as an internal standard (IS) protein. ISs can be commercially available proteins, for example casein. Alternatively, ISs are synthesised specifically for use in the invention. In this embodiment of the invention, reference phosphorylated peptides are typically synthesised with the same sequence as some of the phosphorylated peptides that it is desired to quantify but which are enriched in stable heavy isotopes of carbon and nitrogen. The peptides are typically synthesised using solid phase chemistry in which one amino acid is added at a time to form an amino acid chain or polypeptide. Typically, such peptides are enriched in $^{13}C$ and $^{15}N$ that substitute the common $^{12}C$ and $^{14}N$. This enrichment results in the reference phosphorylated peptides being approximately 6 to 10 daltons heavier than the endogenous phosphorylated peptides with the same sequence so that they can be distinguished using a mass spectrometer.

In another embodiment of the invention, when acetylated peptides are being quantified, the reference modified peptides are reference acetylated peptides. Such reference acetylated peptides are typically synthetic peptide containing acetylated amino acids.

The reference modified peptides (typically reference phosphorylated peptides) are typically added at a known amount in each of the samples to be compared. The signals of the endogenous modified peptides (typically phosphorylated peptides) are normalised to the signal of the reference modified peptides (typically reference phosphorylated peptides) in downstream analysis.

In one embodiment, step (a) of this embodiment further comprises enriching modified peptides (typically phosphorylated peptides) from the mixture of peptides and reference modified peptides (typically reference phosphorylated peptides) obtained in step (a) to produce a mixture of enriched modified peptides (typically phosphorylated peptides). This additional step thus results in a single mixture of enriched modified peptides (typically phosphorylated peptides) per sample. In this embodiment of the invention, step (b) thus comprises carrying out mass spectrometry (MS) on the mixture of enriched modified peptides (typically phosphorylated peptides) to obtain data relating to the peptides in the sample. In this embodiment of the invention, step (a) typically results in a mixture of enriched modified peptides (typically phosphorylated peptides).

The step of enriching modified peptides (typically phosphorylated peptides) is typically carried out using chromatography. In one embodiment, the chromatography is immobilized metal ion affinity chromatography (IMAC), titanium dioxide ($TiO_2$) chromatography, and/or zirconium dioxide ($ZrO_2$) chromatography. Typically, the chromatography is IMAC and $TiO_2$ chromatography.

Alternatively, the step of enriching modified peptides (typically phosphorylated peptides) is carried out using antibody-based methods.

In one embodiment of the invention, when the peptides being quantified are phosphorylated peptides, antibodies with affinity to phosphorylated amino acids such as tyrosine, threonine, serine or histidine are linked (immobilised) to a solid matrix. Phosphorylated peptides are enriched by the ability of these antibodies to specifically bind phosphorylated peptides. Non-phosphorylated peptides are then washed away while phosphorylated peptides are retained on the antibody coated matrices. Elution of phosphorylated peptides from the immobilised antibody is typically carried out using low pH solvents or by any other suitable method that denatures the interaction between antibody and phosphorylated peptides.

In another embodiment of the invention, when the peptides being quantified are acetylated peptides, acetylated peptides are enriched by the use of specific antibodies against acetylated amino acid residues. Such antibodies are linked to a solid matrix and then enriched by the ability of the antibodies to specifically bind acetylated amino acid residues. Non-acetylated peptides are then washed away while acetylated peptides are retained on the immobilised antibody.

In step (b) of this embodiment, mass spectrometry (MS) is carried out on the mixture of peptides and reference modified peptides (typically reference phosphorylated peptides) obtained in step (a) to obtain data relating to the peptides in the sample. Typically, this data is in the form of an MS datafile for the sample. In one embodiment of the invention, when step (a) of this embodiment further comprises enriching modified peptides (typically phosphorylated peptides) from the mixture of peptides and reference modified peptides (typically reference phosphorylated peptides) obtained in step (a) to produce a mixture of enriched modified peptides (typically phosphorylated peptides), step (b) comprises carrying out mass spectrometry (MS) on said mixture of enriched modified peptides (typically phosphorylated peptides) to obtain data relating to the peptides in the sample, typically an MS datafile for the sample. Typically, the mass spectrometry is liquid chromatography-mass spectrometry (LC-MS). Step (b) thus typically results in an LC-MS datafile (one from each sample).

The data relating to the peptides in the sample typically comprises the mass to charge (m/z) ratio, charge (z) and/or relative retention time of the peptides.

In step (c) of this embodiment, the data relating to the peptides in the sample (typically in the form of an MS datafile and more typically an LC-MS datafile) is compared with data in a database of modified peptides (typically phosphorylated peptides) using a computer programme. For example, the mass to charge (m/z) ratio, charge (z) and relative retention time of the peptides in the sample are compared with the mass to charge (m/z) ratio, charge (z) and relative retention time of the modified peptides (typically phosphorylated peptides) in the database. This enables the identification and quantification of each modified peptide (typically phosphorylated peptide) in the sample using the database of modified peptides (typically phosphorylated peptides).

Typically, the computer programme is the programme termed PESCAL (Cutillas, P. R.; Vanhaesebroeck, B. *Mol Cell Proteomics* 6(9), 1560-73, 2007). PESCAL constructs extracted ion chromatograms (XIC, i.e, an elution profile) for each of the modified peptides (typically phosphorylated peptides) present in the database across all the samples that are to be compared. This is done by centring the XIC on the m/z and retention time of the peptide previously identified to be modified (typically phosphorylated) (i.e, present in the database constructed in the first step of the procedure). PESCAL also considers the charge of the peptide to help in the correct assignment of identity. The program also calculates the peak height and area under the curve of each XIC. The data is normalised by dividing the intensity reading (peak areas or heights) of each modified peptides (typically phosphorylated peptide) that is being analysed by those of the reference modified peptides (typically reference phosphorylated peptides).

In this embodiment, the database of modified peptides is compiled by a method comprising the following steps:
i obtaining peptides from a sample;
ii enriching modified peptides from the peptides obtained in step i;
iii carrying out liquid chromatography-tandem mass spectrometry (LC-MS/MS) on the enriched modified peptides obtained in step ii;
iv comparing the modified peptides detected in step iii to a known reference database in order to identify the modified peptides; and
v compiling data relating to the modified peptides identified in step iv into a database.

If the database is a database of phosphorylated peptides, it is compiled by a method comprising the following steps:
i obtaining peptides from a sample;
ii enriching phosphorylated peptides from the peptides obtained in step i;
iii carrying out liquid chromatography-tandem mass spectrometry (LC-MS/MS) on the enriched phosphorylated peptides obtained in step ii;
iv comparing the phosphorylated peptides detected in step iii to a known reference database in order to identify the phosphorylated peptides; and
v compiling data relating to the phosphorylated peptides identified in step iv into a database.

Step i of this embodiment involves obtaining peptides from a sample. Peptides can be obtained from the sample using any suitable method known in the art and as described herein.

The sample is typically a biological sample and can thus be any type of sample obtained from a biological source, as described above. Typically, the sample is a cell line or a tissue.

In some embodiments of the invention, where the sample used in step i is a cell line, the sample is treated with an inhibitor prior to carrying out step i. The inhibitor can be any suitable type of inhibitor. Typically, when phosphorylated peptides are being quantified, the inhibitor is a phosphatase inhibitor. Treatment with phosphatase inhibitors increases the stoichiometry of phosphorylation and results in a greater number of phosphorylated peptides that can be included in the database. In addition, methyl transferase or acetyl hydrolase inhibitors can be used when the purpose is to quantify methylated and acetylated peptides, respectively.

In one embodiment, step i of this embodiment of the method of the invention comprises:
(1) lysing cells in a sample;
(2) extracting the proteins from the lysed cells obtained in step (1); and
(3) cleaving said proteins into peptides.

These aspects of the invention are as described above. However, step (3) is typically carried out using the same method as in the embodiment of the second aspect of the invention described above where a mixture of peptides is obtained from a mixture of proteins by digestion.

In step ii of this embodiment, modified peptides (typically phosphorylated peptides) are enriched from the peptides obtained in step i. Step ii thus results in several fractions enriched in modified peptides (typically phosphorylated peptides).

The enrichment of modified peptides (typically phosphorylated peptides) in step ii is typically carried out using multidimensional chromatography. In one embodiment, the multidimensional chromatography is carried out using strong cation exchange high performance liquid chromatography (SCX-HPLC), immobilized metal ion affinity chromatography (IMAC) and titanium dioxide ($TiO_2$) chromatography. In another embodiment, the multidimensional chromatography is carried out using anion exchange high performance liquid chromatography (SAX-HPLC), immobilized metal ion affinity chromatography (IMAC) and titanium dioxide ($TiO_2$) chromatography. In these embodiments of the invention, the chromatographical techniques are carried out sequentially.

Alternatively, the enrichment of modified peptides (typically phosphorylated peptides) in step ii is carried out using antibody-based methods.

In one embodiment, where the peptides being quantified are phosphorylated peptides, antibodies with affinity to phosphorylated amino acids such as tyrosine, threonine, serine or histidine are linked to a solid matrix. Phosphorylated peptides are enriched by the ability of these antibodies to specifically bind phosphorylated peptides. Non-phosphorylated peptides are then washed away while phosphorylated peptides are retained on the antibody coated matrix. Elution of phosphorylated peptides from the immobilized antibody is typically carried out using low pH solvents or by any other suitable method that denatures the interaction between antibody and phosphorylated peptides.

In another embodiment of the invention, when the peptides being quantified are acetylated peptides, acetylated peptides are enriched by the use of specific antibodies against acetylated amino acid residues. Such antibodies are linked to a solid matrix and then enriched by the ability of the antibodies to specifically bind acetylated amino acid residues. Non-acetylated peptides are then washed away while acetylated peptides are retained on the antibody coated matrix.

In step iii of this embodiment, liquid chromatography-tandem mass spectrometry (LC-MS/MS) is carried out on the enriched modified peptides (typically phosphorylated peptides) obtained in step ii.

In step iv of this embodiment, the modified peptides (typically phosphorylated peptides) detected in step iii are compared to a known reference database in order to identify the modified peptides (typically phosphorylated peptides). This step is typically carried out using a commercially available search engine, such as, but not restricted to, the MASCOT, ProteinProspector, or Sequest search engines.

In step v of this embodiment, data relating to the modified peptides (typically phosphorylated peptides) identified in step iv is compiled into a database. This database lists all the parameters needed for the quantification of phosphorylated peptides in subsequent biological experiments. Typically, the data relating to the modified peptides (typically phosphorylated peptides) includes identity of the modified peptides (typically phosphorylated peptide), mass to charge (m/z) ratio, charge and/or relative retention time. This allows data relating to the peptides in the sample, typically the mass to charge (m/z) ratio, charge (z) and relative retention time of the peptides in the sample, to be compared to the values for the modified peptides (typically phosphorylated peptides) in the database and thus allows the identification and quantification of the modified peptides (typically phosphorylated peptides) in the sample.

In this embodiment, the compilation of the database does not need to be carried out simultaneously with the method of the first or second aspect of the invention. The compilation of the database can be carried out separately, in advance of the TIQUAS technique being used in the method of the invention to quantify the modification (typically phosphorylation) of the peptide at each different concentration of the non-protein substrate (for the first aspect of the invention) or the first substrate (for the second aspect of the invention).

The basis of the TIQUAS technique is the construction of a database of modified peptides (typically phosphorylated peptides) that can be detected and quantified by LC-MS. This database lists all the parameters needed for the quantification of modified peptides (typically phosphorylated peptides) in subsequent biological experiments including the identity of the modified peptide (typically phosphorylated peptide), mass to charge ratio (m/z), charge, and relative retention time. The database can be constructed by enriching modified peptides (typically phosphorylated peptides) using multidimensional chromatography (such as strong cation exchange, IMAC and $TiO_2$). Fractions of enriched modified peptides (typically phosphorylated peptides) can then be analysed by LC-MS/MS for identification of modified peptides (typically phosphorylated peptides).

The computer program named PESCAL (Cutillas and Vanhaesebroeck, *Molecular & Cellular Proteomics* 6, 1560-1573 (2007)) automates the quantification of each of the modified peptides (typically phosphorylated peptides) listed in the database in LC-MS runs of modified peptides (typically phosphorylated peptides) taken from biological experiments. For these biological experiments, proteins in cell lysates are digested using trypsin or other suitable proteases. Peptide (such as phosphopeptide) internal standards, which are reference modified peptides (typically reference phosphorylated peptides), are spiked at known amounts in all the samples to be compared. Modified peptides (typically phosphorylated peptides) in the resultant peptide mixture are enriched using a simple-to-perform IMAC or $TiO_2$ extraction step. Enriched modified peptides (typically phosphorylated peptides) are analysed in a single LC-MS run of typically but not restricted to about 120 minutes (total cycle). PESCAL then constructs extracted ion chromatograms (XIC, i.e, an elution profile) for each of the modified peptides (typically phosphorylated peptides) present in the database across all the samples that are to be compared. The program also calculates the peak height and area under the curve of each XIC. The data is normalised by dividing the intensity reading (peak areas or heights) of each modified peptide (typically phosphopeptide) analyte by those of the modified peptide (typically phosphopeptide) ISs.

As an alternative to using the TIQUAS technique, in the method of the second aspect of the invention, quantification of modifications such as phosphorylation can also be carried out using MS techniques that use isotope labels for quantification, such as metabolic labeling (e.g., stable isotope labeled amino acids in culture, (SILAC); Olsen, J. V. et al. *Cell* 127, 635-648 (2006)), and chemical derivatization (e.g., iTRAQ (Ross, P. L.; et al. *Mol Cell Proteomics* 2004, 3, (12), 1154-69), ICAT (Gygi, S. P. et al. *Nat Biotechnol* 17, 994-999 (1999)), TMT (Dayon L et al, Anal Chem. 2008 Apr. 15; 80(8):2921-31) techniques. In the method of the invention, modifications such as phosphorylation can be quantified with LC-MS techniques that measure the intensities of the unfragmented ions or with LC-MS/MS techniques that measure the intensities of fragment ions (such as Selected Reaction Monitoring (SRM), also named multiple reaction monitoring (MRM)).

Step (iii) of the method of the second aspect of the invention comprises determining the affinity of the enzyme (such as a protein kinase) for the first substrate. A high affinity of the enzyme (such as a protein kinase) for the first substrate is indicative of the polypeptide being an in vivo substrate of the enzyme (such as a protein kinase).

The method of the second aspect of the invention can be used to simultaneously determine the affinity of an enzyme for the first substrate, i.e. the non-protein substrate of the enzyme or a mixture of polypeptides, in relation to numerous peptides. The affinity of the enzyme for the first substrate for each of the peptides can then be ranked and it can be determined which of the peptides are in vivo substrates of the enzyme. Modification events that demonstrate high affinity for the first substrate are more likely to occur in vivo, which allows the identification of modification sites that are real physiological substrates.

The method of the second aspect of the invention can therefore be used to simultaneously determine the affinity of a protein kinase for the first substrate, i.e. ATP or a mixture of polypeptides, in relation to numerous peptides, in other words for numerous phosphosites. The affinity of the protein kinase for the first substrate for each of the peptides (phosphosites) can then be ranked and it can be determined which of the peptides are in vivo substrates of the protein kinase. Phosphorylation events that demonstrate high affinity for the first substrate are more likely to occur in vivo, which allows the identification of phosphorylation sites that are real physiological substrates.

The affinity of the enzyme (for example protein kinase) for the first substrate, for example ATP, can be determined using the principles of Michaelis-Menten kinetics. For example, an affinity constant (Ac, related to Km) can be calculated for each peptide, as shown in FIG. 2A. FIG. 2B shows two representative responses; a) a protein kinase activity with high affinity for ATP (low Ac) and b) a protein kinase activity with low affinity for ATP (high Ac).

In one embodiment, step (iii) of the method of the second aspect of the invention comprises:
  (a) determining whether modification of the peptide is increased when the concentration of the first substrate is increased; and, if modification of the peptide is increased when the concentration of the first substrate is increased;
  (b) calculating the affinity constant (Ac) of the enzyme for the first substrate.

In this embodiment, when the enzyme is a protein kinase, step (iii) comprises:
  (a) determining whether phosphorylation of the peptide is increased when the concentration of the first substrate is increased; and, if phosphorylation of the peptide is increased when the concentration of the first substrate is increased;
  (b) calculating the affinity constant (Ac) of the protein kinase for the first substrate.

The measurement of the Ac allows the ranking of identified substrates according to the affinity of enzyme (such as protein kinase) reactions to said substrates. Substrates of low Ac are more likely to be in vivo substrates of the enzyme (such as a protein kinase) under investigation.

As set out above, MS-based phosphoproteomic analysis has great potential as a method to allow rapid and accurate quantification of signalling pathway activities. Such data would be invaluable for the investigation and development of treatments for a wide range of diseases that results from disruption to signalling pathways. However, MS-based phosphoproteomics is currently limited as the kinases responsible for the phosphorylation events investigated are not usually known. In order for this field to reach its full potential it is necessary to accurately annotate the phosphoproteome with the identities of the kinases that control each phosphorylation event.

The present inventors have developed a strategy that couples an in-vitro kinase assay to quantitative phosphoproteomics to enable shotgun identification of phosphorylation events downstream of protein kinases. Taking Akt1 as a paradigm, this approach enabled the identification of over 100 potential substrates downstream of this kinase, many of which have not previously been described. In order to improve the accuracy of this strategy the inventors also defined a measure of the affinity of Akt1 for ATP for each phosphorylation site. This constant termed Ac, is based on Michaelis-Menten enzyme kinetics principles. Ac was used to group phosphopeptides into those with high affinity for ATP (low Ac) and those with low affinity for ATP (high Ac) and it was proposed that phosphosites with low Ac were most likely to be true in vivo substrates of Akt1. Motif analysis of these two groups revealed that, indeed, phosphopeptides with low Ac were enriched for motifs that correspond with the consensus phosphorylation motif of Akt1 and, thus, were likely to be bona fide substrates.

This strategy can be applied to identify substrates for any kinase and thus can provide great advances in the field of investigation into signalling pathway activities. The method of the invention has advantages over methods known in the art because traditional methods for the investigation of kinase activity often require the use of radioactively-labelled ATP and thus their use is limited by practical considerations. In addition, many of these methods also require lengthy purification processes to enable substrate identification and thus are very expensive and time-consuming. The method of the second aspect of the present invention overcomes such limitations. An additional consideration is that other techniques usually result in the identification of one or just a few kinase substrates whereas the inventors' method has the potential to identify more than 100 potential substrates at a time. A further advantage of this method over existing techniques is that it is able to provide a level of confidence for the identification of substrates by measuring the affinity of the kinase-substrate reaction.

The method of the second aspect of the present invention has a number of applications. In addition to annotating the phosphoproteome, the method can be used to identify downstream targets of specific kinases. These readouts thus may serve as biomarkers of kinase activities of kinases and have applications as pharmacodynamic markers and also as markers of disease and prognosis. In addition, novel substrates identified may reveal potential novels drug targets for specific diseases.

Preferred features for the first aspect of the invention are as for the second aspect mutatis mutandis.

Preferred features for the second aspect of the invention are as for the first aspect mutatis mutandis.

Figure 1B:
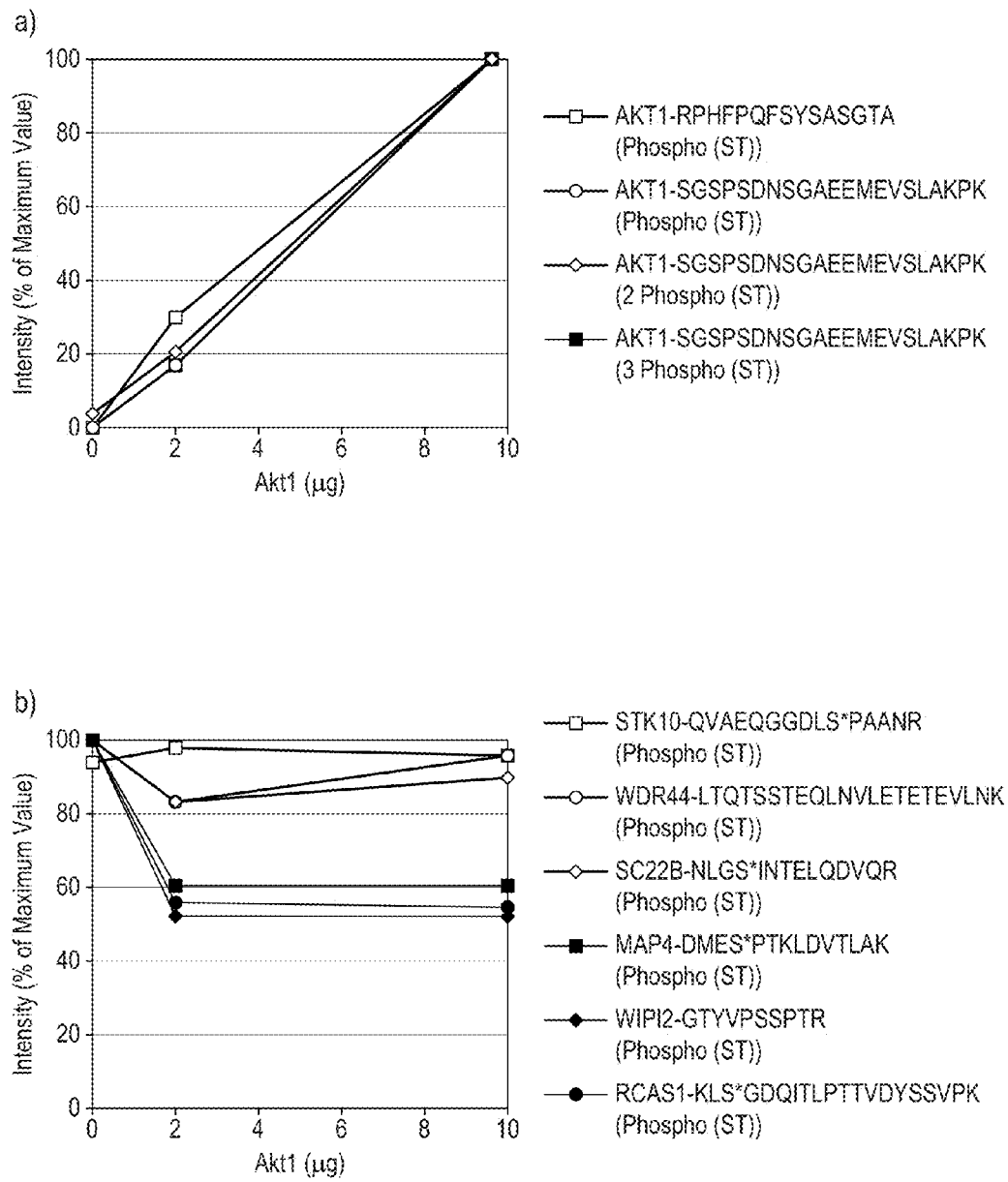
Figure 1B:
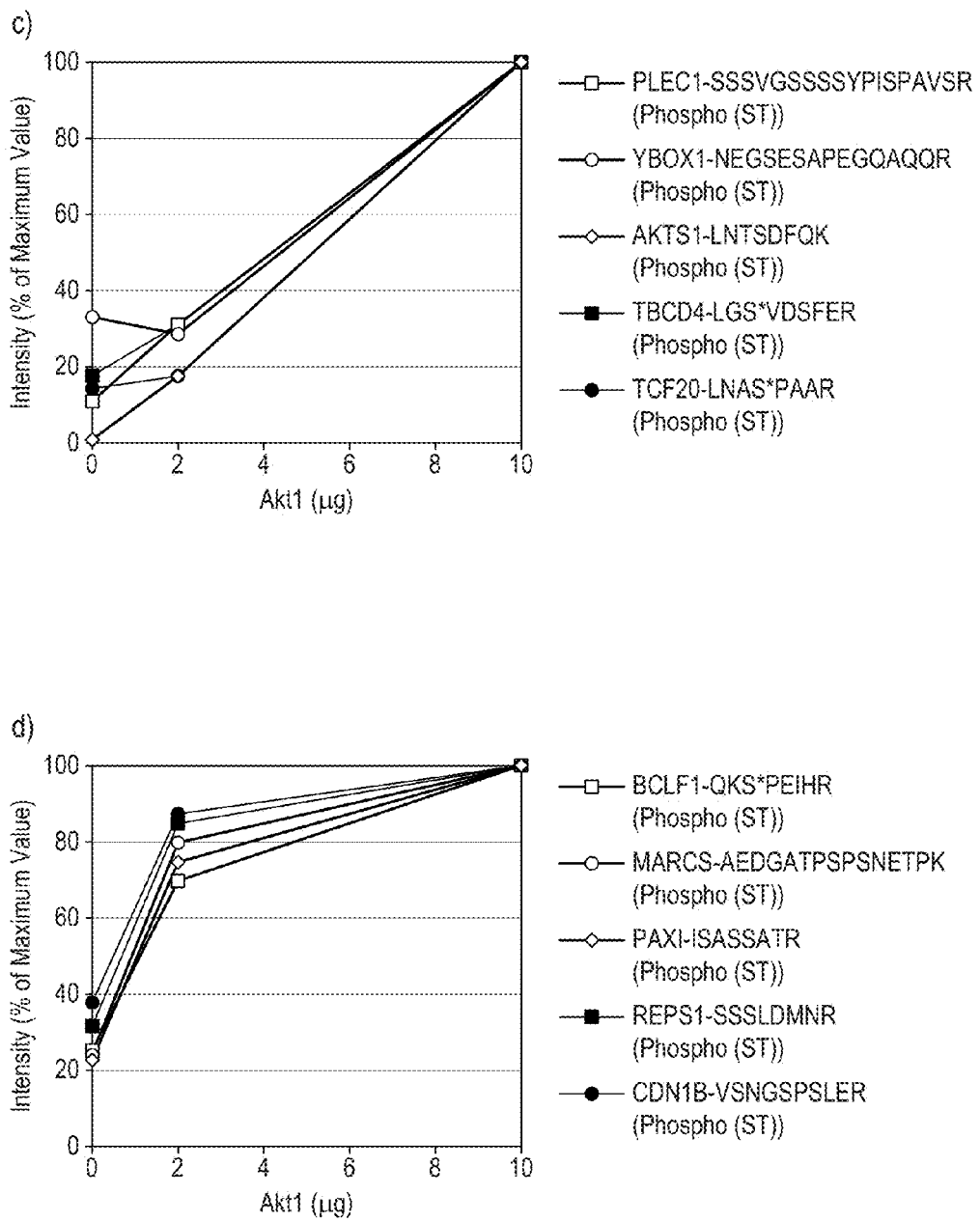

The present invention will now be further described by way of reference to the following Examples which are present for the purposes of illustration only. In the Examples, reference is made to a number of Figures as follows:

FIG. 1: Dynamics of peptide phosphorylation varied in response to increasing concentrations of Akt1. The phosphorylation dynamics of 561 peptides in response to increasing concentrations of active Akt1 in an in vitro kinase assay were evaluated using quantitative phosphoproteomics. A. Normalized phosphopeptide intensity heatmap for all 561 peptides illustrated the diversity of phosphorylation responses to Akt1 encountered. B. Detailed illustration of phosphorylation responses for representative groups of peptides. a) Phosphorylation of Akt1, which served as internal control for the experiment. b) Phosphorylation of a representative group of peptides that showed no, or decreased, response to Akt1 activity. c) Phosphorylation of a representative group of peptides that demonstrated an approximately linear response, thus indicating that they were likely to be phosphorylated downstream of Akt1. d) Phosphorylation of a representative group of peptides that demonstrated a rapid, sustained response, thus indicating that they were also likely to be phosphorylated downstream of Akt1. 124 phosphopeptides were identified across groups c) and d).

FIG. 2: Calculation of Akt1-ATP affinity. A. Using the principles of Michaelis-Menten kinetics and a variation of the Hanes-Woolf plot an Affinity Constant (Ac) was defined for the activity of Akt1 towards ATP for each phosphorylation site. B. Examples of two representative responses. a) An Akt1 activity with high affinity for ATP (low Ac). b) An Akt1 activity with relatively low affinity for ATP (high Ac). Of the phosphopeptides evaluated, 51.7% were found to have Akt1 activities with low Ac (<50 µM, n=108) and 48.3% were found to have Akt1 activities with high Ac (>49 µM, n=101) for ATP.

Figure 3A:
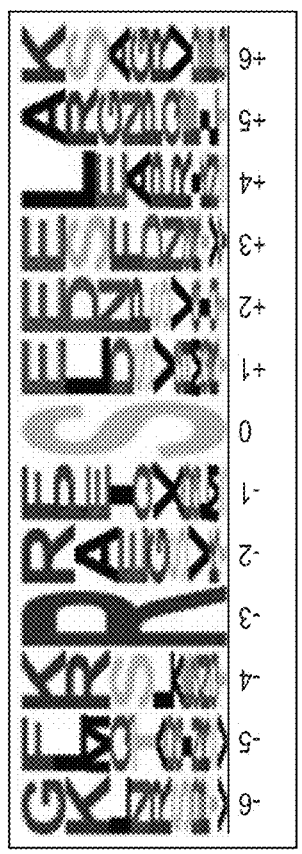
Figure 3B:
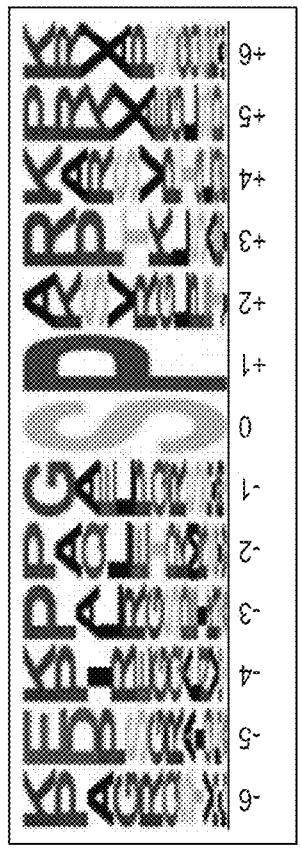
Figure 3B:
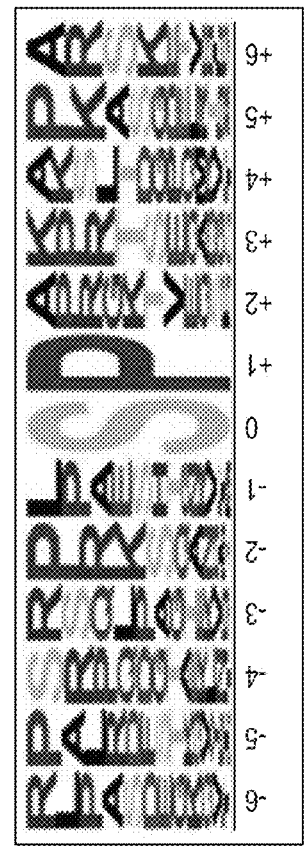

FIG. 3: Motif analysis revealed that phosphopeptides with low Akt1-ATP Ac were enriched for basophilic motifs. Motif-X analysis of phosphopeptides from groups A. Ac<50 µM (high affinity for ATP) and B. Ac>49µ (M low affinity for ATP) revealed that group A was enriched for basophilic motifs, which corresponds to the consensus phosphorylation motif of Akt1 (Alessi, D. R. et al., Molecular basis for the substrate specificity of protein kinase PKB; comparison with MAPKAP kinase-1 and p70 S6 kinase. FEBS, 1996. 399: p. 333-338).

FIG. 4 shows the strategy for Global Profiling of Kinase Activities (GKAP) by mass spectrometry. (a) Scheme for the GKAP workflow. ATP and Mg2+ are added to cell free extracts and kinase reactions allowed to occur in which endogenous kinases phosphorylate endogenous protein substrates. The products of such enzymatic reactions are digested with trypsin, and phosphopeptides obtained as a result enriched by TiO2 using optimized techniques {Montoya et al, Methods. 2011 August; 54(4):370-8}. Phosphopeptides containing sites of phosphorylation produced as a result of kinase activity are then detected and quantified by LC-MS/MS. (b) Example of the quantification of a kinase activity on the peptide with the sequence shown (asterisk denoted the site of modification) on Serine/threonine-protein kinase MST4 at position 173. Extracted ion chromatogram (XIC) at m/z 878.9299 shows an increase in activity as a function of ATP concentration. Blue, red and green curves correspond to the XICs of the first, second and third isotope of this peptide, respectively. (c) Normalized activity on the peptides shown in (b). (d) Mean normalized intensities of all activities detected in the assay. (e) Number of activities detected in P31/Fuj as a function of ATP concentration in the assay. (f) Patters of kinase activities as a function of protein amounts and ATP concentrations in the assay. (g) Examples of activities detected in 5 µg of cell lysate. All values are the mean of duplicate measurements.

FIG. 5 shows Global Profiling of Kinase Activities in leukemia cell lines of different sensitivity to kinase inhibitors. (a) The GKAP approach was applied to P31/Fuj and Kasumi-1 at the concentrations of ATP shown Kinase activities were normalized to the greatest value for each phosphopeptide. (b, c, d) Examples of activities are shown as kinetic curves (left panels) or as areas under the curve (AUC, left panels) of the activities in left panels.

FIG. 6 shows Global Profiling of Kinase Activities downstream of growth factors and kinase inhibitors. (a) The GKAP approach was applied to epithelial cells at the concentrations of ATP shown after treatment with EGF, or with EGF and LY92004 or U0126. Kinase activities were normalized to the greatest value for each phosphopeptide. (b) Number of activities detected in each experimental condition in (a). (c, d, e, f) Examples of activities are shown as kinetic curves (left panels) or as areas under the curve (AUC, left panels) of the activities in left panels.

Figure 7A:
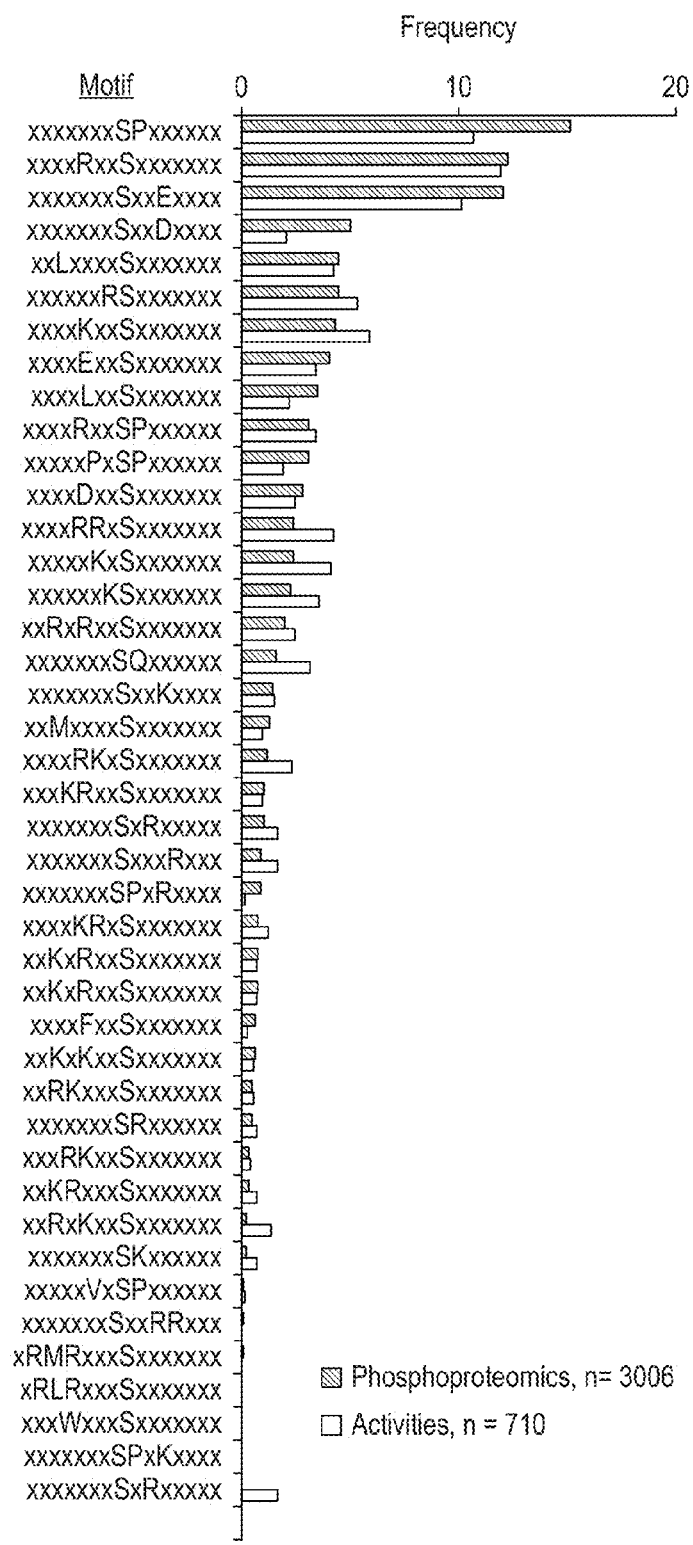
Figure 7B:
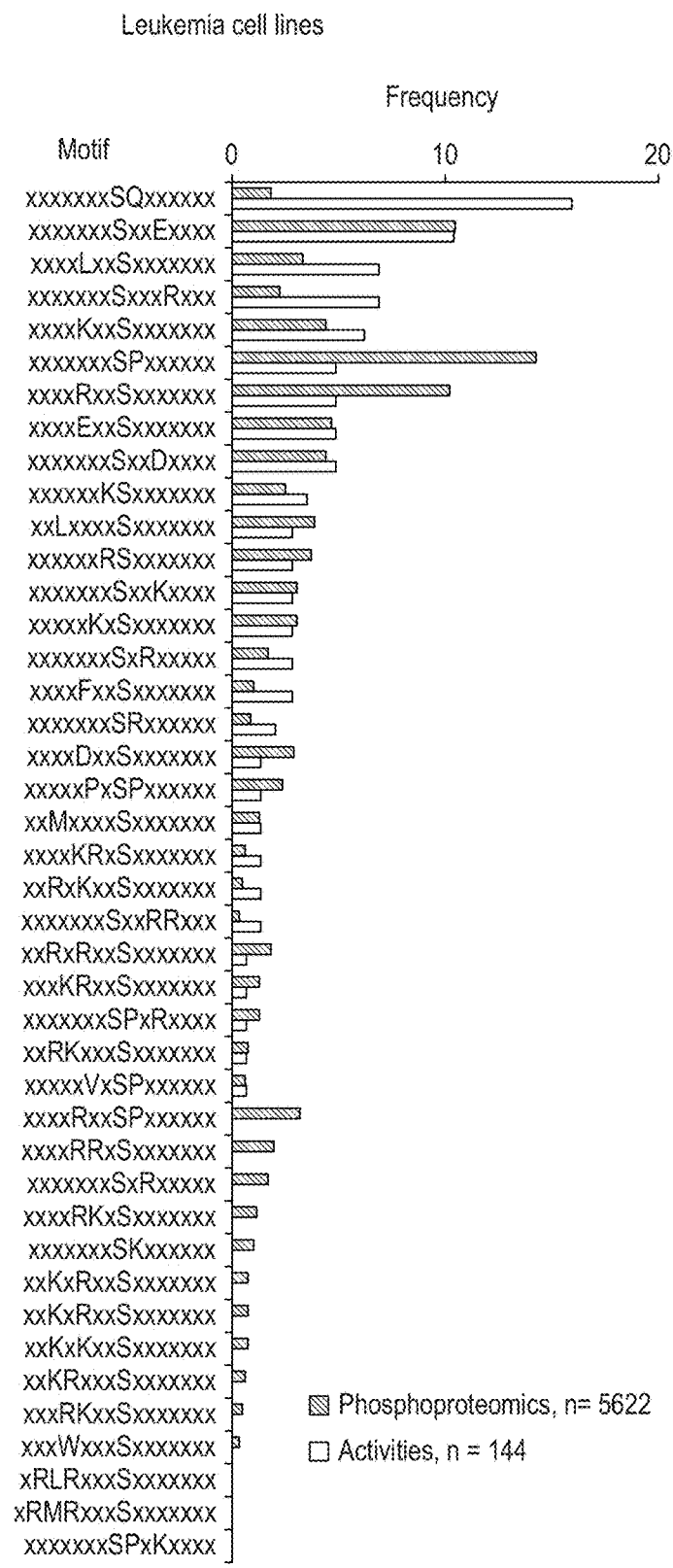

FIG. 7: Comparative analysis of phosphorylation motifs obtained from GKAP or phosphoproteomics experiments. A total of 44 motifs were matched to phosphopeptides markers of GKAP activities or to those obtained from phosphoproteomics experiments. The results for the epithelial cell line and leukemia cells are shown in (a) and (b), respectively. For simplicity, "S" denotes either phosphoserine or phosphothreonine as the phosphorylated central amino acid in the motif. Note that a given peptide may contain more than one motif.

EXAMPLE 1

Identification of Substrates of the Protein Kinase Akt1

Introduction

The present inventors have developed a strategy that combines an in-vitro kinase assay, adapted from the protocol described by Cartlidge et al (2005)[1], with MS-based shotgun phosphoproteomics to enable the investigation of phosphorylation events dependent on a specific kinase. In brief; total cell lysate was depleted of small molecules (including ATP) using size exclusion chromatography and then de-phosphorylated by exploiting the endogenous phosphatase activity of the sample. The de-phosphorylated sample, which served as the in vitro assay substrate, was then incubated with recombinant, active kinase under controlled reaction conditions. Samples were subsequently subjected to in-solution trypsin digestion and phosphopeptides were then partially purified using titanium dioxide chromatography. Enriched phosphopeptides (containing the sites of modification by the kinase of interest) were then identified and quantified by LC-MS/MS and LC-MS analysis using a ThermoFisher LTQ-Orbitrap XL. The approach of Targeted In-Depth Quantification of Signalling (TIQUAS) was used to perform these quantifications and to investigate the dynamics of phosphorylation sites under different reaction conditions (ATP concentrations).

This strategy was applied to identify substrates of the protein kinase Akt1. Over 100 peptides that are phosphorylated downstream of Akt1 in-vitro were identified. Using the principles of Michaelis-Menten kinetics an Affinity Constant (Ac) was defined for the activity of Akt1 towards ATP for each site, thus allowing the identification of phosphorylation sites that are more likely to be dependent on this kinase in-vivo (i.e., in cells under physiological conditions). Motif analysis confirmed that high affinity activity of Akt1 towards proteins occurs on sites surrounded by basic amino acids, which corresponds with the known consensus phosphorylation motif of this kinase[2].

Materials and Methods

Cell Culture

MCF10A human mammary epithelial cells were cultured in humidified incubators kept at 37° C. with 5% $CO_2$ in DMEM:Hams F12 (1:1) medium supplemented with 1% penicillin and streptomycin, 5% horse serum, 20 ng/ml EGF, 0.5 µg/ml hydrocortisone, 100 ng/ml cholera toxin and 10 µg/ml insulin.

Cell Lysis

Cells were washed twice with ice-cold PBS before lysis with 40 mM Tris-HCl pH 7, 1% Triton X-100 and 2.5 mM EDTA supplemented with protease inhibitors (15 mM DTT, 1 mM phenylmethylsulfonyl fluoride (PMSF), 10 µg/ml aprotinin, 10 µg/ml leupeptin). Cells were scraped and vortexed thoroughly before incubation on ice for 20 minutes. The resulting lysate was then clarified by centrifugation at 13,000 rpm for 10 minutes at 4° C.

Akt1 Kinase Assay

Cell lysate was depleted of small molecules by size exclusion filtration, using Sephadex G-25 (GE healthcare 28-9180-07) columns and 40 mM Tris-HCl pH 7.0, 1 mM DTT, 0.1 mM EGTA and 0.1% Triton X-100 elution buffer. Lysate was then left at 30° C. for 20 minutes for protein dephosphorylation by endogenous phosphatases[3].

1 mg of dephosphorylated lysate was then diluted in reaction buffer to a final concentration of 50 mM Tris-HCl pH 7.5, 1 mM EGTA, 1 mM DTT, 10 mM $MgCl_2$ and 0-500 µM $ATP^2$. Recombinant, active Akt1 (Millipore 14-276) was then added and the mixture incubated at 30° C. for 10 minutes. The reaction was stopped by the addition of urea to a final concentration of 8 M.

In-solution Trypsin Digestion and Phosphopeptide Enrichment

Proteins were reduced by incubation with 10 mM DTT for 15 minutes at room temperature and alkylated by incubation with 16.6 mM iodoacetamide (IAM) for a further 15 minutes at room temperature. Samples were then diluted 1 in 4 with 20 mM HEPES buffer (pH 8) and proteins digested by incubation with immobilized, TPCK-treated trypsin (Thermo Scientific) for 16 hours at 37° C.

Peptide samples were de-salted by reversed-phase solid phase extraction using Oasis HLB Cartridges (Waters WAT094225) using conditions optimized in our laboratory.

Chromatographic purification of phosphopeptides was carried out by incubation of samples with $TiO_2$ beads (Titanspheres, GL Sciences 5020-7500) prior to washing with buffers of compositons optimized in our laboratory and elution with 5% $NH_4OH$ (pH 11).

Phosphopeptide solutions were acidified and dried under vacuum prior to reconstitution in 0.1% trifluoroacetic acid (TFA) for MS analysis.

Mass Spectrometry Analysis

LC-MS and LC-MS/MS analysis was carried out using a ThermoFisher LTQ-Orbitrap XL, equipped with an electrospray source, coupled to a Waters NanoAcquity UPLC System. Peptides were separated on this system using a Waters BEH130 (Ethylene Bridged Hybrid) C18 reverse-phase column (100 µm×100 mm), packed with 1.7 µm particles, and an increasing gradient of ACN. MS ddata was acquired in data-dependent mode, performing MS scans in the orbitrap analyzer and acquiring MS/MS scans of the 5 most abundant ions detected by sequential isolation, CID fragmentation and detection in the LTQ ion trap.

Data Analysis

For phosphopeptide identification, Mascot Distiller (Matrix Science) was used to extract MS peak data from MS data files. The search engine MASCOT (Matrix Science) was then used to identify peptides and proteins by comparison of MS/MS spectra data against the theoretical MS/MS of all peptide entries in the human SwissProt database.

Phosphopeptides were quantified using Pescal (a computer program developed in house) using the principles of TIQUAS.

The online software Motif-X (http://motif-x.med.harvard.edu/) was used to extract common phosphorylation motifs from submitted phosphopeptide data.

Results

Identification of Phosphosites Dependent on Akt1

Dephosphorylated MCF10A cell lysate was subjected to the described in vitro kinase assay using 0, 2 or 10 µg of recombinant active Akt1 protein kinase and 100 µM ATP, prior to trypsin digestion, phosphopeptide enrichment and MS analysis. Quantitative analysis of MS data was used to identify phosphorylation events likely to be dependent on Akt1.

561 phosphopeptides were identified to the required level of confidence (MASCOT expectancy scores <0.05) across the three samples. TIQUAS was used to quantify the dynamics of phosphorylation of these sites under different reaction conditions of concentrations of Akt1 (FIG. 1A). Quantification of phosphopeptides of Akt1 itself served as an internal control for the experiment (FIG. 1B a)) and validated the quantitative approach. Many phosphopeptides were identified that did not respond to increasing concentrations of Akt1 or demonstrated a decrease (FIG. 1B b)). These phosphorylation events were likely to be dependent on kinases and phosphatases endogenous to the sample and thus were not affected by Akt1 concentration. Peptides that showed at least a 1.5 fold increase in phosphorylation when incubated with 10 µg Akt1 compared to when incubated with 0 µg Akt1 were considered to be dependent on this kinase and thus likely to be downstream substrates. This group was further sub-divided into those that showed an approximately linear response to Akt1 (FIG. 1B c)) and those that showed a more rapid and sustained response (FIG. 1B d)), which therefore have a higher affinity for Akt1 and are more likely to be authentic substrates in vivo. 124 phosphopeptides were identified as likely to be downstream of Akt1 thus identifying many potential novel substrates of this kinase.

Characterisation of the Affinity of Akt1-Dependent Phosphosites for ATP

In order to identify which of the potential Akt1-dependent phosphorylation events were most likely to occur in vivo an approach was devised to quantify the affinity of Akt1 for ATP in relation to each phosphorite. Phosphorylation events that demonstrate high affinity for ATP are more likely to occur in vivo thus permitting us to rank candidate substrates by their probability to be real physiological substrates. A dephosphorylated MCF10A cell lysate was subjected to the described in vitro kinase assay but this time 0, 10, 50, 100 or 500 µM ATP was used for incubations with 2 µg of Akt1 for 10 minutes. As before, this kinase reaction was followed by trypsin digestion, phosphopeptide enrichment and MS analysis. Quantitative analysis of MS data was used in conjunction with the principles of Michaelis-Menten kinetics to define an Affinity Constant (Ac, related to Kin) for the activity of Akt1 towards ATP for each phosphosite (FIG. 2A).

Affinity Constant (Ac), as defined in FIG. 2A, was calculated for all the phosphopeptides that were found to be elevated in response to increasing concentrations of ATP in this assay (n=245). We considered phosphopeptides with Ac<50 μM as demonstrating high Akt1-ATP affinity and those with Ac>49 μM as demonstrating low Akt1-ATP affinity (FIG. 2B). Of the phosphopeptides evaluated, 51.7% were found to have Akt1 activities with low Ac (<50 μM, n=108) and 48.3% were found to have Akt1 activities with high Ac (>49 μM, n=101) for ATP. Phosphopeptides with low Ac are most likely to be true in vivo substrates of Akt1 whereas phosphopeptides with high Ac are more likely to be an artefact of the in vitro assay.

Validation of Phosphopeptide Classification

Motif-X was used to analyze the consensus phosphorylation motifs for phosphopeptides with low and high Akt1-ATP Ac (FIG. 3) in order to validate the classification of phosphopeptides. Analysis revealed that the group of phosphopeptides with Ac<50 μM (high affinity for ATP) was enriched for basophilic motifs, which corresponds to the known consensus phosphorylation motif of Akt1 RxRxxS/T[2]. Thus, motif analysis validated the hypothesis that phosphopeptides with high Akt1-ATP affinity are more likely to be bona fide Akt1 substrates in vivo.

References
1. Cartlidge, R. A., et al., The tRNA methylase METTL1 is phosphorylated and inactivated by PKB and RSK in vitro and in cells. EMBO J, 2005. 24(9): p. 1696-1705.
2. Alessi, D. R. et al., Molecular basis for the substrate specificity of protein kinase PKB; comparison with MAP-KAP kinase-1 and p70 S6 kinase. FEBS, 1996. 399: p. 333-338.
3. Knebel, A., N. Morrice, and P. Cohen, A novel method to identify protein kinase substrates: eEF2 kinase is phosphorylated and inhibited by SAPK4/p38[delta]. EMBO J, 2001. 20(16): p. 4360-4369.

EXAMPLE 2

Global Profiling of Protein Kinase Activities by Mass Spectrometry

Materials and Methods

Materials. Cell culture reagents were purchased from Invitrogen. Other reagents were purchased as indicated: recombinant human EGF (Peprotech AF-100-15), LY294002 (Merck 440202), U0126 (Merck 662005), PI103 (Merck 528100), JAK inhibitor I (Merck 420099), Adenosine 5'-triphosphate disodium salt hydrate (ATP) (Sigma A2383), TLCK-trypsin (Thermo Scientific 20230), Oasis HLB extraction cartridges (Waters WAT094225), $TiO_2$ titanspheres (GL Sciences Inc 5020-75010), PepClean C-18 Spin Columns (Thermo Scientific 89870), MTS assay (CellTiter 96®AQueous One Solution Cell Proliferation assay, Promega Corporation, G3581).

Cell Culture. All cells were maintained at 37° C. in a humidified atmosphere at 5% $CO_2$. The leukemia cell lines P31/Fuj and Kasumi-1 were grown in RPMI-1640 medium supplemented with 10% FBS, 100 units/mL of penicillin/streptomycin and 50 μM β-mercaptoethanol. Cells were maintained between 0.5 and $2\times10^6$ cells/mL. 24 h prior to harvest, $50\times10^6$ cells were seeded at a density of $0.5\times10^6$ cells/mL in fresh medium.

The immortalized breast epithelial cell line MCF10A was grown in DMEM:F12 (1:1) medium supplemented with 5% horse serum, 100 units/mL of penicillin/streptomycin, 20 ng/ml EGF, 0.5 μg/ml hydrocortisone, 100 ng/ml cholera toxin and 10 μg/ml insulin. Prior to growth factor and inhibitor treatments the cells were maintained for 18 h in DMEM:F12 (1:1) supplemented with 100 units/mL of Penicillin/Streptomycin alone. Cells were then treated with 5 μM LY294002 or 10 μM U0126 for 1 h prior to stimulation with 100 ng/ml recombinant EGF for 10 min.

Proliferation Assays. P31/Fuj and Kasumi-1 cell lines were seeded in 96 well plates at a concentration of $1\times10^5$ cells per mL ($1\times10^4$ cell per well). After 24 h recovery, cells were treated with vehicle (DMSO), 100 nM PI-103, 1μM JAK inhibitor I or 10μM U0126. After 72 h treatment, cell viability was measured using an MTS assay following the manufacturer's protocol. Each condition was analyzed 5 times. t-tests was used to determine differences between cell lines. Differences were considered statistically significant when p-value <0.05.

Cell Lysis for GKAP. MCF10A cells and leukemia cells (collected by centrifugation at 300 × g for 5 min) were washed twice with ice-cold phosphate buffered saline supplemented with phosphatase inhibitors (1 mM $Na_3VO_4$ and 1 mM NaF). Cells were then lysed in 40 mM Tris-HCl pH 7.4, 1% Triton X-100 and 2.5 mM EDTA supplemented with protease inhibitors (0.05 TIU/mg aprotinin, 10 μM leupeptin, 0.7 mM pepstatin A, 27 μM TLCK, 1 mM DTT and 1 mM PMSF) and phosphatase inhibitors (50 mM NaF, 1 mM $Na_3VO_4$ and 1 μM okadaic acid). Cell lysates were further homogenized by vortexing and insoluble material was removed by centrifugation at 20,000×g for 10 min. Protein concentration in the supernatants was calculated by Bradford analysis.

In vitro GKAP Assay. Total cell lysate, containing the required amount of protein (50 μg where not indicated), was mixed with 1:1 in reaction buffer producing a final reaction mix concentration of 40 mM Tris-HCl pH 7.4, 1.25 mM EDTA, 10 mM $MgCl_2$ and ATP as indicated (0-500 μM). The assay mixture was then incubated, with mixing, at 30° C. for 5 min. The reaction was stopped by the addition of urea to a final concentration of 8 M prior to further processing for phosphoproteomic LC-MS/MS analysis.

Cell Lysis for Phosphoproteomics. MCF10A cells and leukaemia cells (collected by centrifugation at 300×g for 5 min) were washed twice with ice-cold phosphate buffered saline supplemented with phosphatase inhibitors (1 mM $Na_3VO_4$ and 1 mM NaF). Cells were then lysed and proteins denatured in 8 M urea, 20 mM HEPES (pH 8.0) supplemented with phosphatase inhibitors (1 mM Na3VO4, 1 mM NaF, 2.5 mM Na4P2O7, 1 mM β-glycerol-phosphate). Cell lysates were further homogenized by sonication and insoluble material was removed by centrifugation at 20,000×g for 10 min. Protein concentration in the supernatants was calculated by Bradford analysis and samples of cell lysates containing 500 μg of protein were further processed for phosphoproteomic LC-MS/MS analysis.

In-solution Digestion and $TiO_2$ Affinity Chromatography for Phosphoproteomic Analysis. In-solution trypsin digestion and phosphopeptide enrichment using $TiO_2$ affinity chromatography was performed as described by Montoya et al[1]. In brief, samples were reduced and alkylated by sequential incubation with DTT and iodoacetamide and diluted with 20 mM HEPES (pH 8.0) buffer to 2 M urea prior to incubation with TLCK-trypsin for 16 h. Digestion was stopped by addition of trifluoroacetic acid (TFA) to a final concentration of 1% and samples were desalted by solid phase extraction. Phosphopeptides were then extracted from samples by affinity chromatography with 25 µl of TiO$_2$ beads (50% slurry) packed in spin columns and eluted with 5% NH$_4$OH (pH ~11.0). Phosphopeptide-enriched samples were then acidified with formic acid, dried using a Speedvac and pellets stored at −80° C. until analysis.

LC-MS and LC-MS/MS. LC-MS and LC-MS/MS analysis was performed as previously described [1,2]. In brief, peptide pellets were dissolved in 12 µl of 0.1% TFA and run in a LTQ-Orbitrap XL mass spectrometer (Thermo Fisher Scientific, Hemel Hempstead, UK) coupled online to a nanoflow ultra-high pressure liquid chromatography (UPLC, nanoAcquity, Waters). Peptide separations were performed in a BEH 100 µm×100 mm column (Waters) using solution A (0.1% FA in LC-MS grade water) and solution B (0.1% FA in LC-MS grade ACN) as mobile phases. Full scan survey spectra were acquired in the Orbitrap and data dependent analysis (DDA) was employed in which the 5 most abundant multiply charged ions present in the survey spectrum (MS) were automatically mass-selected, fragmented by collision-induced dissociation and analyzed in the LTQ (MS/MS). The mass accuracy of MS1 spectra was calibrated on-line by the use of the background ion at m/z 445.1200 for lock-mass correction.

Data Analysis. Data Analysis was performed as described [1,2]. In brief, Mascot Daemon (v2.2.2; Matrix Science, London, UK) was used to analyze the MS data. This software automated the use of Mascot Distiller (v2.3.2.), to smooth and centroid the MS/MS data, and Mascot search engine (v2.2.02), to search the processed files against all entries in the peptide sequence library of the Swiss Prot database (downloaded on Mar. 3, 2011 containing 23000 entries). Search parameters included: enzyme, trypsin; number of missed cleavages permitted, 2; fixed modification, Carbamidomethyl (C); variable modifications, Gln->pyro-Glu (N-term Q), Oxidation (M), Phospho (ST), Phospho (Y); mass tolerance for precursor ions, 5 ppm; mass tolerance for fragment ions, 0.6 Da. Hits were considered significant when they had an Expectation value<0.05 (as returned by Mascot). An in-house script was used to extract Mascot results, which were then placed in Excel files for further analysis. For peptides with multiple potential phosphorylation sites, the delta score between the first and second hits reported by Mascot was used to identify the correct position[3]. Pescal[4] was used to automate the generation of extracted ion chromatograms (XIC) and to calculate the peak heights across samples. XICs were constructed for the first three isotopes of each peptide ion, allowing the application of restrictions on the m/z, tR, charge and isotope distribution. The intensity values could then be calculated by determining the peak height of each individual XIC. The resulting quantitative data were parsed into Excel files for normalization and statistical analysis. Peptide intensities in samples incubated with ATP were normalized to their intensities in control samples (without incubation).

Results

We aimed to test the idea that protein kinase activities may be more efficiently and comprehensively assayed by using full length proteins as substrates for in-vitro kinase reactions. In the technique reported here (FIG. 4a), protein kinases present in cell lysates are allowed to phosphorylate endogenous substrates also present in the cell lysate after the addition of ATP to the cell free extract (and cofactors needed for kinases to be active). After incubation during a defined period of time, reaction products are then quantified using standard phosphoproteomic techniques based on quantitative mass spectrometry[1, 2, 5]. We also envisaged that by performing the assay at different concentrations of ATP, this would allow the assessment of enzymatic properties of kinases across experimental conditions for each of the activities being monitored.

Figure 4A:
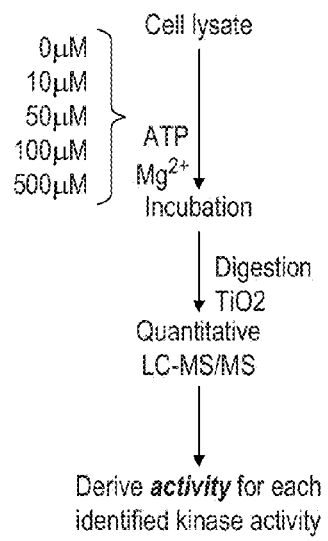
Figure 4B:
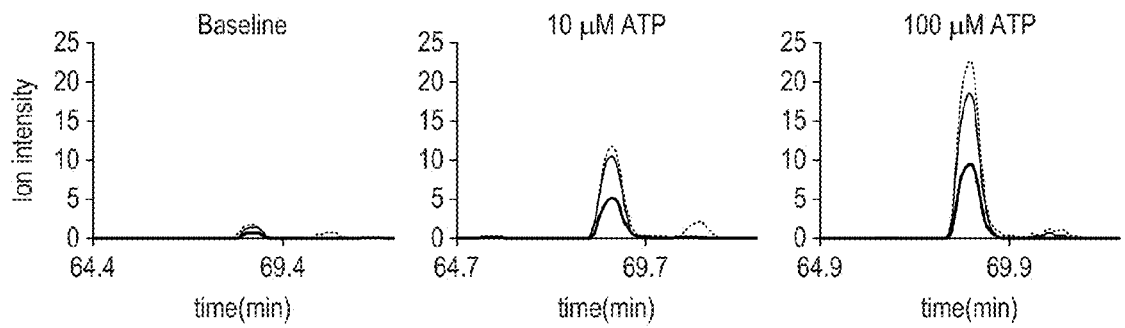
Figure 4C:
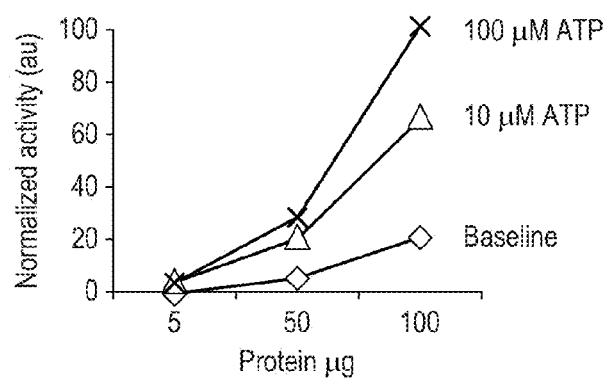
Figure 4D:
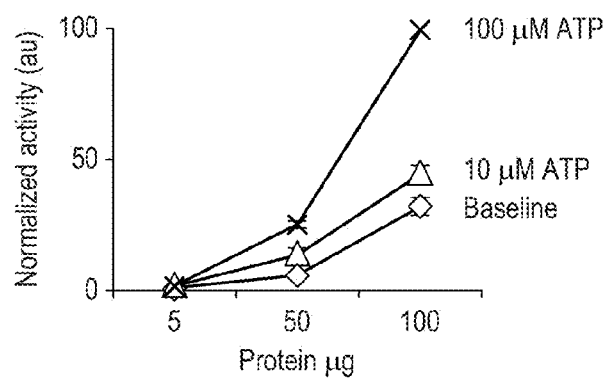
Figure 4E:
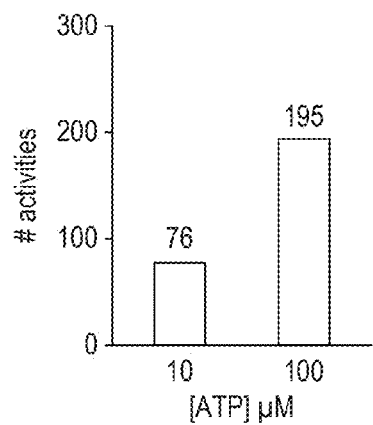
Figure 4F:
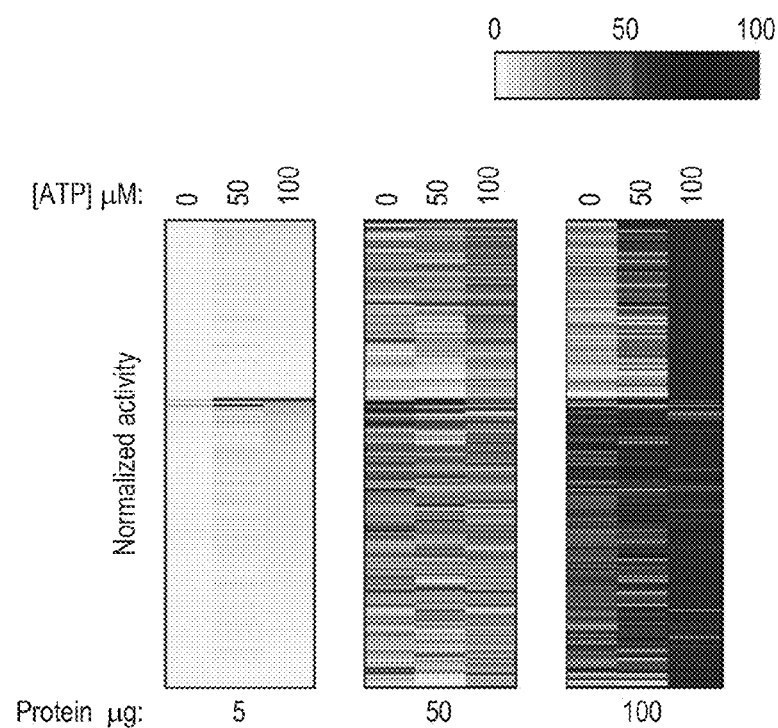
Figure 4G:
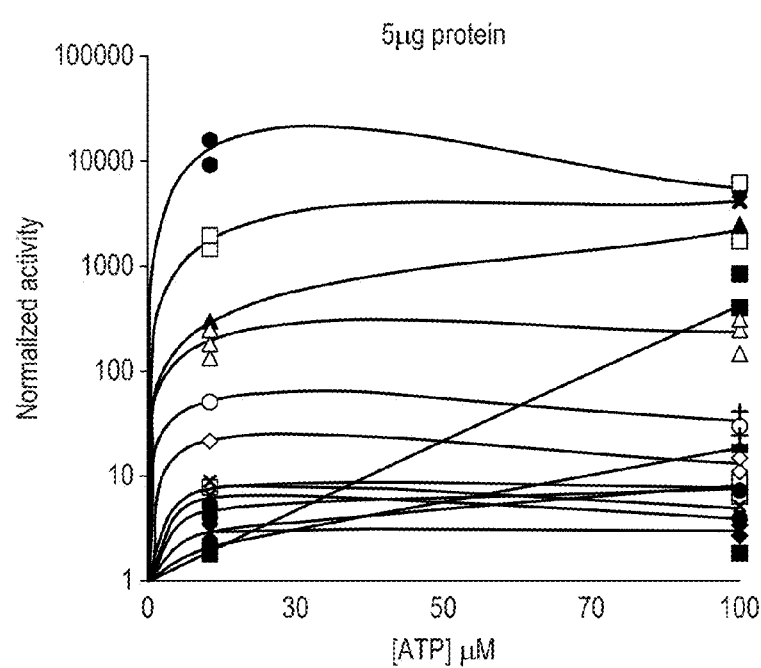

We first incubated different protein amounts in a cell lysate obtained from P31/Fuj (a leukaemia cell line) with reaction buffer containing different concentrations of ATP (0 µM, 10 µM or 100 µM) and different concentrations of total cell lysate (as measured by protein concentration). The data obtained with the approach can be illustrated with the analysis one reaction product on MST4 (sequence LADFGVAGQLTDT*QIK, where the asterisk denotes the phosphorylated amino acid) (FIG. 4b). The extraction ion chromatograms of this phosphopeptide revealed that its intensity increased when just 5 µg of protein in a total cell lysate was incubated with increasing concentrations of ATP (FIG. 4b) thus exemplifying the amplification of signal inherent in activity assays, a feature that make them very sensitive. FIG. 4c shows a plot of normalized intensities of this phosphopeptide relative to its basal phosphorylation levels as a function of ATP and protein concentration, while FIG. 4d shows the normalized mean intensities of all the activities measured in this experiment. Activity was defined as a 2 fold increase on phosphopeptide signal after incubation with ATP over its signal in the non-incubated sample. Using this criterion, 76 and 195 activities were identified in these cells after incubation with 10 and 100 µM ATP, respectively (FIG. 4e-f) thus further confirming that kinase activities, as obtained by GKAP, increase as a function of ATP concentration. As expected, these activity measurements were also proportional to protein amounts in the reaction mixture (FIG. 4f), although even at just 5 µg of protein in the cell lysate>100 kinase reactions were detected, examples of which are shown in FIG. 4h.

Figure 5A:
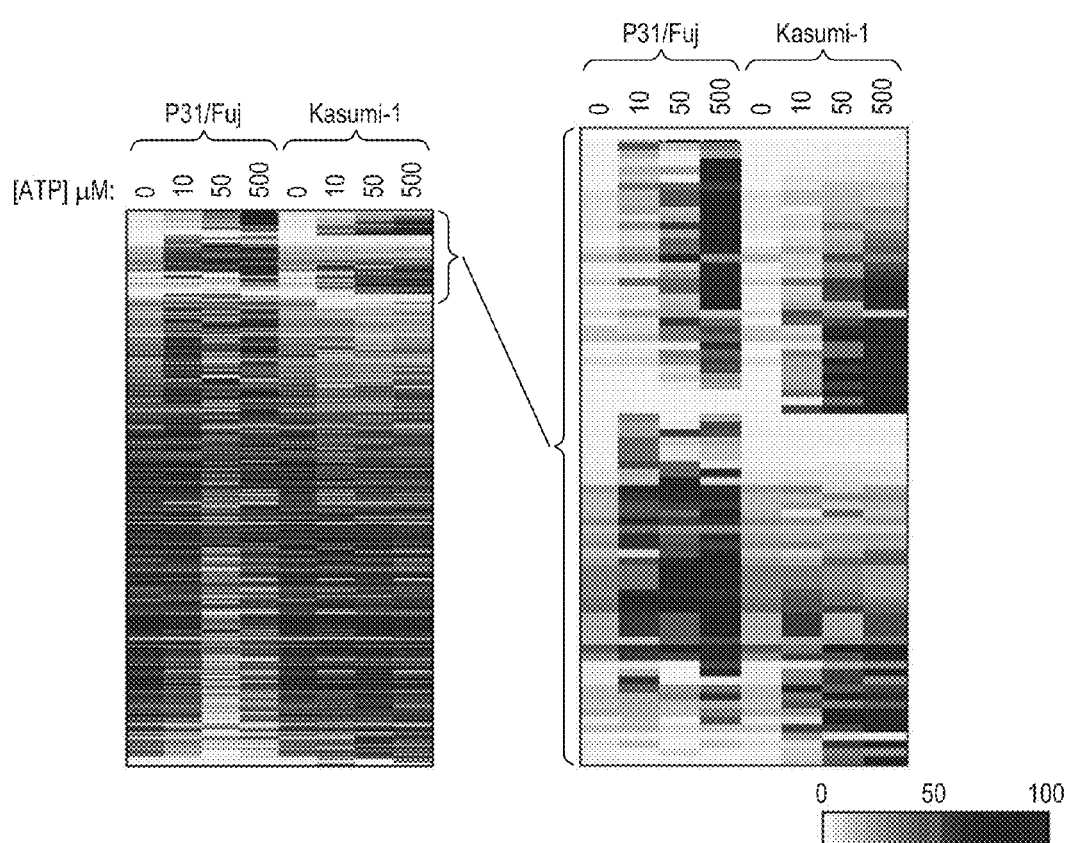
Figure 5B:
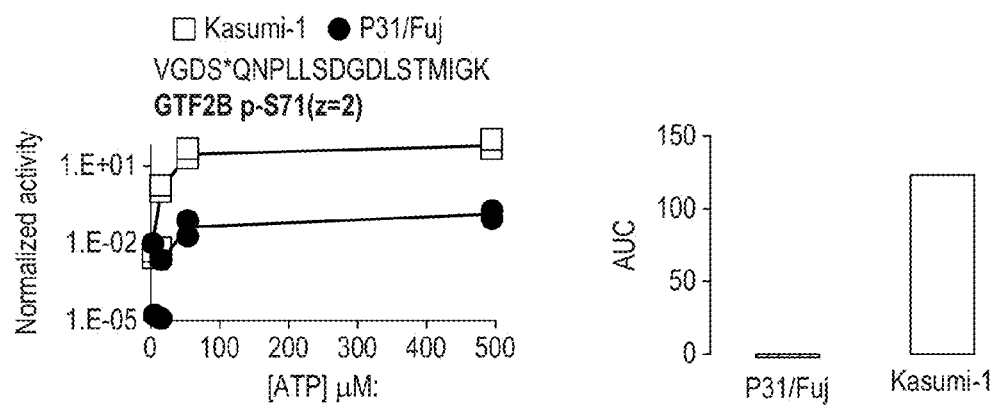
Figure 5C:
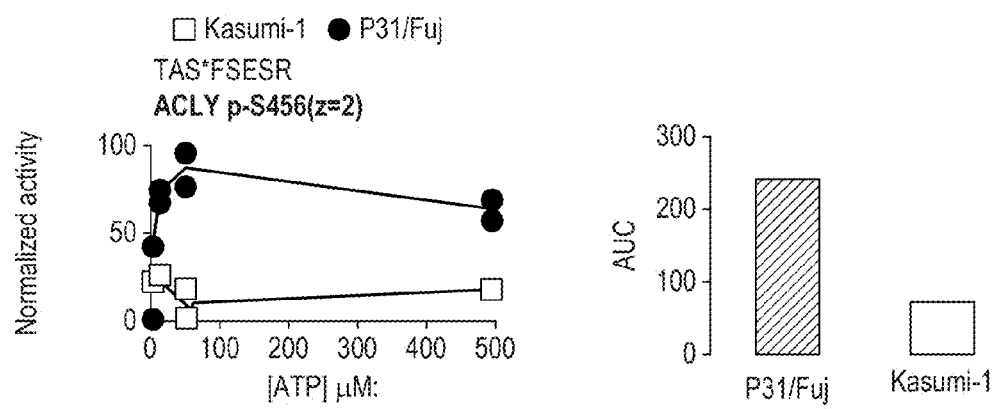
Figure 5D:
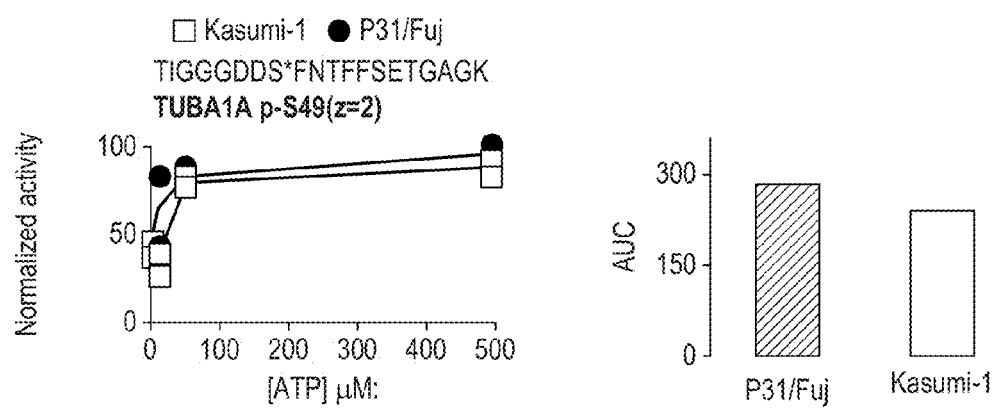

We next investigated whether different cancer cells exhibited detectable differences in kinase activities. For this, we chose to apply GKAP to P31/Fuj and Kasumi-1, two leukaemia cell lines which show markedly different patterns of proliferation sensitivity to MEK, JAK, Scr and PI3K inhibitors, with P31/Fuj being more resistant to inhibition of proliferation than Kasumi-1 when treated with these compounds[2]. Using the same criteria for defining a kinase reaction outlined above, our analysis uncovered 81 kinase reactions in these leukaemia cell lines that were proportional to ATP concentration (FIG. 5a). Examples of these activities are given in FIGS. 5b, 5c and 5d, for activities that were either increased in Kasumi-1, P31/Fuj or were unchanged, respectively. The left panels of FIGS. 5b, 5c and 5d show activities as a function of ATP concentration, while right panels show the area under the curve (AUC) for each of these kinase activity profiles. These results thus show that GKAP can be used to detect differences in signaling pathway activation in cancer cells of different phenotype and of distinct sensitivity to targeted compounds.

Figure 6A:
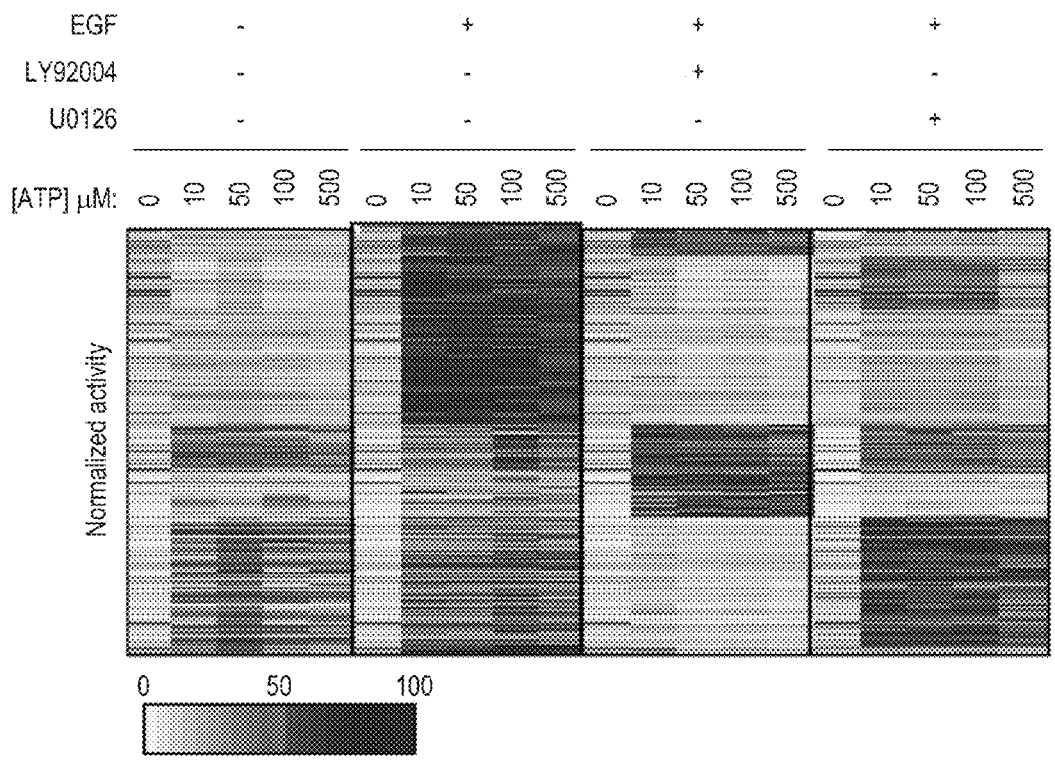
Figure 6B:
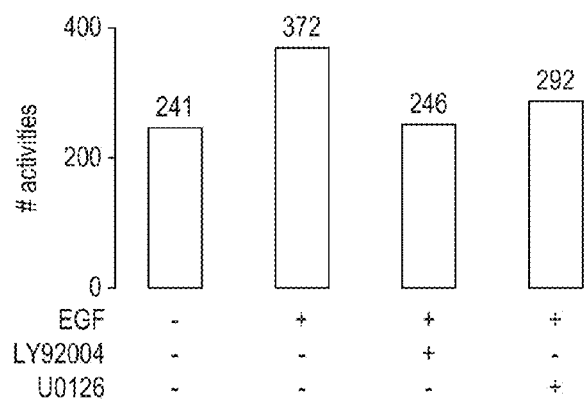
Figure 6C:
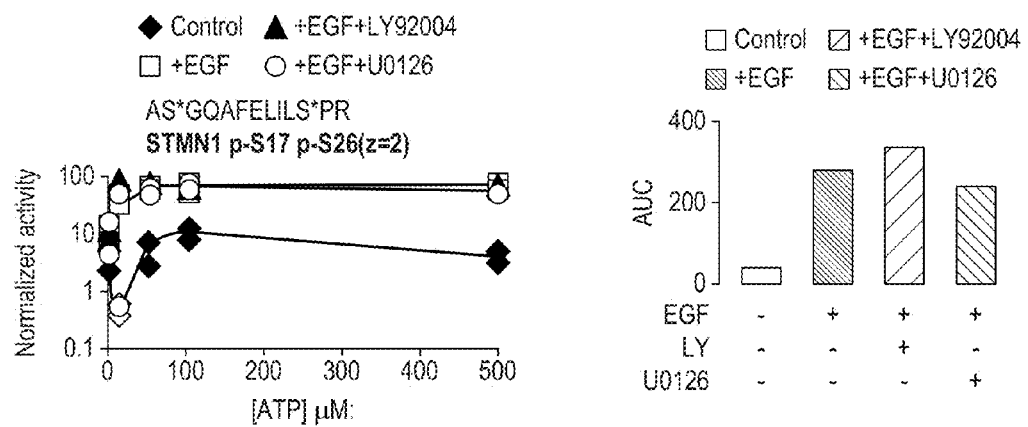
Figure 6D:
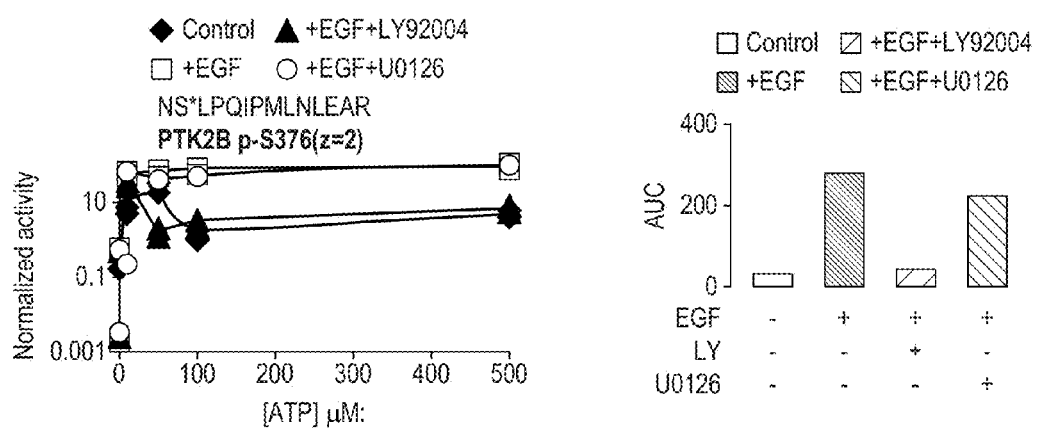
Figure 6E:
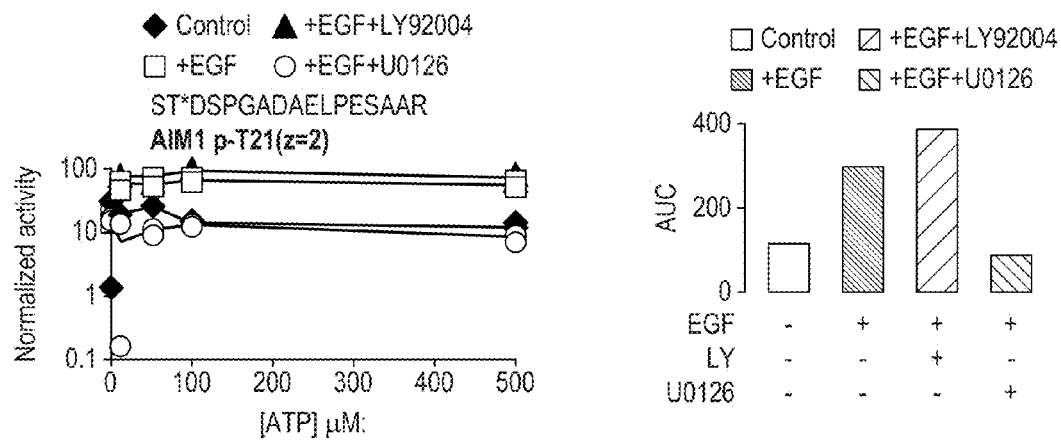
Figure 6F:
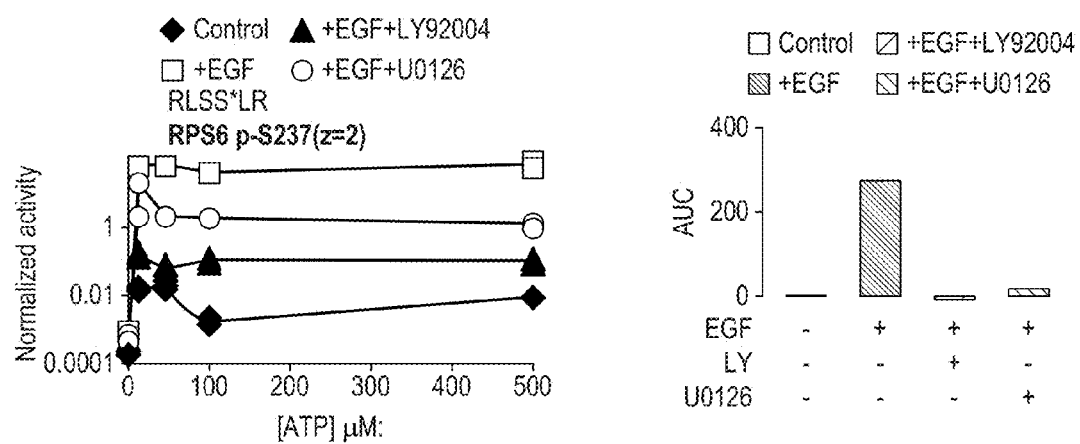

We then asked the question of whether kinase activities, as quantified by GKAP, may be modulated as a result of stimuli known to affect kinase pathways and can thus provide readouts of pathway activation. This question was addressed by applying the GKAP workflow to the epithelial cell line MCF10A after treatment with EGF, a growth factor known to activate several kinase pathways downstream of its receptor. Cells were also pre-treated with inhibitors against PI3K and MEK, namely LY92004 and U0126 respectively, before treatment with EGF. For these experiments, GKAP was performed at four different ATP concentrations (10, 50, 100 and 500 µM) and the intensities of quantified phosphopeptides expressed as fold over basal phosphorylation (no incubation, shown as 0 µM ATP in FIG. 6). FIG. 6a shows the patterns of kinase activities affected by EGF, LY92004 and U0126. More than 240 kinase activities were detected in untreated starved cells (FIG. 6b); this number increased to 372 when cells were treated with EGF (a 1.54 fold increase). Both kinase inhibitors decreased about 30% the number of EGF-dependent kinase activities that were detected in these experiments (FIG. 6b). Examples of kinase activities quantified in these experiments are given in FIG. 6c-f, which depict that the activities as a function of ATP concentration followed sigmoid curves typical of enzyme kinetics (FIG. 6c-f, left panels); right panels in FIG. 6c-f show the AUC of these kinase activities. An example of activity that was increased upon EGF stimulation but was unaffected by pre-treatment with kinase inhibitors is shown in FIG. 6c. Examples of kinase activities decreased by LY92003, U0126 or both are shown in FIGS. 6d, 6e and 6f, respectively. Interestingly, the activities downstream of kinases affected by LY92004 and U0126 (FIGS. 6d and 6e) were superimposed to the activities in control cells, indicating that the contribution of off-target kinases to these activities was negligible.

The experiments described above show that GKAP can be used to profile several hundred kinase activities in a kinetic fashion. However, the utility of the approach is clearly dependent on these activities being contributed by different kinases rather than just a few of them phosphorylating all peptides detected in the assay. Although this not the only determinant in coffering specificity, different kinases phosphorylate their substrates in the context of linear motifs surrounding the site of phosphorylation[6]. Therefore, an assessment of the different motifs being phosphorylated in a GKAP experiment could be used to infer the repertoire of kinases that contribute to the observed activities. We compiled a list of 44 motifs known to be phosphorylated by different kinases from the literature[6] and matched them to our dataset of kinases activities. For comparison, we also performed large-scale phosphoproteomics of the same cell lines used in this study and determined the distribution of motifs present in these basal phosphoproteomes. The analysis revealed that all motifs present in a standard phosphoproteomics experiment were also present in the phosphopeptides used to quantify kinase activity in the epithelial cell line (FIG. 7a) even though the number of phosphorylation motifs obtained by phosphoproteomics was about 4 fold greater than those obtained as activities. Most phosphorylation motifs associated with the leukemia phosphoproteomes were also present as activities (FIG. 7b) although it is interesting to observe that the phosphorylation motifs obtained from activity assays and phosphoproteomics overlapped less in leukemia cells than in epithelial cells.

The results presented above indicate that GKAP is a general method for the analysis of kinase activity as most, if not all, kinase activities expressed in a cell line or tissue should be represented in these assays. This contrast with previous studies that used short peptides as kinase substrates[7,8]; these were based on the addition of selected substrates for specific kinases for in-vitro kinase reactions, thus having the same limitation as antibody-based assays in that a bias was introduced towards the analysis of kinases for which selectivity and specificity towards their substrates were well characterized. Here we have shown that kinase activities can be quantified without a preconception of the kinases that may be active in the biological models under investigation. It may also be argued that for a kinase reaction to occur in cells, the substrates of such kinases have to be expressed in the biological model under study. Indeed, kinase activities for which substrates are not expressed will not have functional consequences regardless of how active the kinase/phosphatase reaction may be [9]. The activities uncovered by GKAP take into account not only intrinsic kinase activity but also substrate expression, both of which contribute to pathway activation. In addition, kinase activities revealed by GKAP assays occur on full-length proteins, which are the physiological substrates of kinases, thus reducing the possibility of un-specific kinases contributing to the measured activities. Although in order to demonstrate the technique here we have used label-free LC-MS as the quantitative readout, labeling methods (*Nat. Biotechnol.* 2007 September; 25(9):1035-44; *Nat. Biotechnol.* 2004 September; 22(9):1139-45. Epub 2004 Aug. 15) could also be used to detect and quantify GKAP products. GKAP is a conceptually simple but generally applicable approach to profile kinase activities in an unbiased and specific fashion and should thus have broad applicability in studies aimed at understanding the mechanisms of signal transduction and for advancing the development of therapies based on signaling inhibitors.

REFERENCES

1. Montoya, A., Beltran, L., Casado, P., Rodriguez-Prados, J.C. & Cutillas, P. R. Characterization of a TiO(2) enrichment method for label-free quantitative phosphoproteomics. *Methods* 54(4):370-378 (2011).
2. Casado, P. & Cutillas, P. R. A self-validating quantitative mass spectrometry method for assessing the accuracy of high-content phosphoproteomic experiments. *Mol Cell Proteomics* 10, M110 003079 (2011).
3. Savitski, M. M. et al. Confident phosphorylation site localization using the Mascot Delta Score. *Mol Cell Proteomics* 10, M110 003830 (2010).
4. Cutillas, P. R. & Vanhaesebroeck, B. Quantitative profile of five murine core proteomes using label-free functional proteomics. *Mol Cell Proteomics* 6, 1560-1573 (2007).
5. Bodenmiller B, Wanka S, Kraft C, Urban J, Campbell D, Pedrioli P G, Gerrits B, Picotti P, Lam H, Vitek O, Brusniak M Y, Roschitzki B, Zhang C, Shokat K M, Schlapbach R, Colman-Lerner A, Nolan G P, Nesvizhskii A I, Peter M, Loewith R, von Mering C, Aebersold R. Phosphoproteomic analysis reveals interconnected system-wide responses to perturbations of kinases and phosphatases in yeast. Sci Signal. 2010 Dec. 21; 3(153):rs4. PubMed PMID: 21177495
6. Miller M L, Jensen L J, Diella F, Jørgensen C, Tinti M, Li L, Hsiung M, Parker S A, Bordeaux J, Sicheritz-Ponten T, Olhovsky M, Pasculescu A, Alexander J, Knapp S, Blom N, Bork P, Li S, Cesareni G, Pawson T, Turk B E, Yaffe M B, Brunak S, Linding R. Linear motif atlas for phosphorylation-dependent signaling. Sci Signal. 2008 Sep. 2; 1(35):ra2. PubMed PMID: 18765831
7. Cutillas P R, Khwaja A, Graupera M, Pearce W, Gharbi S, Waterfield M, Vanhaesebroeck B. Ultrasensitive and absolute quantification of the phosphoinositide 3-kinase/ Akt signal transduction pathway by mass spectrometry. Proc Natl Acad Sci USA. 2006 Jun. 13; 103(24):8959-64.
8. Kubota K, Anjum R, Yu Y, Kunz R C, Andersen J N, Kraus M, Keilhack H, Nagashima K, Krauss S, Paweletz C, Hendrickson R C, Feldman A S, Wu C L, Rush J, Villén J, Gygi S P. Sensitive multiplexed analysis of kinase activities and activity-based kinase identification. Nat. Biotechnol. 2009 October; 27(10):933-40.
9. Cutillas P R, Jørgensen C. Biological signalling activity measurements using mass spectrometry. Biochem J. 2011 Mar. 1; 434(2):189-99.

The invention claimed is:

1. A method for identifying differential activation between samples of a protein transferase having a non-protein donor substrate and a protein acceptor substrate;
   said method comprising:
   (i) exposing a first sample to x different concentrations of the non-protein donor substrate of said protein transferase, wherein x is 2 or greater than 2;
   (ii) quantifying modification of a polypeptide in said first sample at each of the x different concentrations of the non-protein donor substrate;
   (iii) determining the affinity of said protein transferase for said non-protein donor substrate;
   (iv) repeating steps (i) to (iii) for a second or subsequent sample; and
   (v) comparing the affinity of said protein transferase for said non-protein donor substrate between said samples;
   wherein a difference in affinity of said protein transferase for said non-protein donor substrate between samples is indicative of differential activation of said protein transferase between samples.

2. The method of claim 1, wherein said sample is a cell lysate.

3. The method of claim 1, wherein a mixture of peptides is obtained from said sample by digestion prior to step (ii).

4. A method for identifying an in vivo substrate of a protein transferase having a non-protein donor substrate and a protein acceptor substrate;
said method comprising:
exposing said protein transferase to x different concentrations of a first substrate, wherein x is 2 or greater than 2, while leaving the concentration of a second substrate constant, wherein one of the first and second substrates is the non-protein donor substrate of said protein transferase and the other is a mixture of polypeptides;
(ii) quantifying modification of a polypeptide in said mixture of polypeptides at each of the x different concentrations of said first substrate; and
(iii) determining the affinity of said protein transferase for said first substrate;
wherein a high affinity of said protein transferase for said first substrate is indicative of said polypeptide being an in vivo substrate of said protein transferase.

5. The method of claim 4, wherein said mixture of polypeptides is a mixture of undigested proteins.

6. The method of claim 5, wherein said mixture of undigested proteins is obtained from a sample by lysing cells in said sample to produce a cell lysate.

7. The method of claim 6, wherein said cell lysate is depleted of small molecules prior to carrying out step (i) and/or wherein said cell lysate is dephosphorylated prior to carrying out step (i).

8. The method of claim 4, wherein said mixture of polypeptides is a mixture of undigested proteins, and wherein a mixture of peptides is obtained from said mixture of undigested proteins by digestion prior to step (ii).

9. The method of claim 4, wherein said mixture of polypeptides is a mixture of peptides that have been obtained by digestion of proteins.

10. The method of claim 3, wherein said peptides are from 5 to 30 amino acids in length.

11. The method of claim 1, wherein:
(a) said protein transferase is a protein kinase and said non-protein donor substrate is ATP; or
(b) said protein transferase is a protein acetyltransferase and said non-protein donor substrate is a compound having an acetyl group; or
(c) said protein transferase is a protein glycosyltransferase and said non-protein donor substrate is an activated nucleotide sugar; or
(d) said protein transferase is a protein methyltransferase and said non-protein donor substrate is a compound having a methyl group; or
(e) said protein transferase is a protein palmitoyltransferase and said non-protein donor substrate is a compound containing the lipid palmitoyl.

12. The method of claim 1, wherein x is at least 3.

13. The method of claim 1, wherein step (ii) is carried out using a method comprising the following steps:
(a) carrying out mass spectrometry (MS) on said sample to obtain data relating to the polypeptide in the sample; and
(b) comparing the data relating to the polypeptide in the sample with data in a database of modified polypeptides using a computer programme;
wherein the database of modified polypeptides is compiled by a method comprising:
i) obtaining polypeptides from a sample;
ii) enriching modified polypeptides from the polypeptides obtained in step i);
iii) carrying out liquid chromatography-tandem mass spectrometry (LC-MS/MS) on the enriched modified polypeptides obtained in step ii);
iv) comparing the modified polypeptides detected in step iii) to a known reference database in order to identify the modified polypeptides; and
v) compiling data relating to the modified polypeptides identified in step iv) into a database.

14. The method of claim 13, wherein step (a) further comprises enriching modified polypeptides from sample to produce a mixture of enriched modified polypeptides and carrying out mass spectrometry (MS) on said mixture of enriched modified polypeptides to obtain data relating to the modified polypeptides in the sample.

15. The method of claim 13, wherein:
the data relating to the polypeptides in the sample is selected from the group consisting of the mass to charge (m/z) ratio, charge (z) and relative retention time of the polypeptides; and/or
said mass spectrometry (MS) in step (b) is liquid chromatography-mass spectrometry (LC-MS); and/or
step (b) ii) is carried out using multidimensional chromatography or antibody-based methods; and/or
step (b) iv) is carried out using the MASCOT search engine; and/or
the data relating to the modified polypeptides is selected from the group consisting of identity of the modified polypeptide, mass to charge (m/z) ratio, charge (z) and relative retention time of the modified peptide.

16. The method of claim 15, wherein the multidimensional chromatography is carried out using:
(a) strong cation exchange high performance liquid chromatography (SCX-HPLC), immobilized metal ion affinity chromatography (IMAC) and titanium dioxide ($TiO_2$) chromatography; or
(b) anion exchange high performance liquid chromatography (SAX-HPLC), immobilized metal ion affinity chromatography (IMAC) and titanium dioxide ($TiO_2$) chromatography.

17. The method of claim 8, wherein said peptides are from 5 to 30 amino acids in length.

18. The method of claim 4, wherein:
(a) said protein transferase is a protein kinase and said non-protein donor substrate is ATP, suitably wherein said protein kinase is a recombinant protein kinase; or
(b) said protein transferase is a protein acetyltransferase and said non-protein donor substrate is a compound having an acetyl group; or
(c) said protein transferase a protein glycosyltransferase and said non-protein donor substrate is an activated nucleotide sugar; or
(d) said protein transferase is a protein methyltransferase and said non-protein donor substrate is a compound having a methyl group; or
(e) said protein transferase is a protein palmitoyltransferase and said non-protein donor substrate is a compound containing the lipid palmitoyl.

19. The method of claim 4, wherein step (ii) is carried out using a method comprising the following steps:
(a) carrying out mass spectrometry (MS) on said mixture of polypeptides to obtain data relating to the polypeptide in the mixture of polypeptides; and
(b) comparing the data relating to the polypeptide in the mixture of polypeptides with data in a database of modified polypeptides using a computer programme;

wherein the database of modified polypeptides is compiled by a method comprising:
  i) obtaining polypeptides from a sample;
  ii) enriching modified polypeptides from the polypeptides obtained in step i);
  iii) carrying out liquid chromatography-tandem mass spectrometry (LC-MS/MS) on the enriched modified polypeptides obtained in step ii);
  iv) comparing the modified polypeptides detected in step iii) to a known reference database in order to identify the modified polypeptides; and
  v) compiling data relating to the modified polypeptides identified in step iv) into a database.

* * * * *